（12） United States Patent
Kannan

(10) Patent No.: US 12,120,514 B2
(45) Date of Patent: Oct. 15, 2024

(54) MULTI-MODAL APPROACH TO A SECURE AND CLOSED SOLUTION FOR PROVIDING SCHEDULED NOTIFICATIONS

(71) Applicant: ARRIS Enterprises LLC, Suwanee, GA (US)

(72) Inventor: Navneeth N. Kannan, Doylestown, PA (US)

(73) Assignee: ARRIS ENTERPRISES LLC, Horsham, PA (US)

( * ) Notice: Subject to any disclaimer, the term of this patent is extended or adjusted under 35 U.S.C. 154(b) by 342 days.

(21) Appl. No.: 17/480,309

(22) Filed: Sep. 21, 2021

(65) Prior Publication Data

US 2022/0201484 A1 Jun. 23, 2022

Related U.S. Application Data

(60) Provisional application No. 63/129,779, filed on Dec. 23, 2020.

(51) Int. Cl.
*H04W 12/084* (2021.01)
*H04W 4/50* (2018.01)
(Continued)

(52) U.S. Cl.
CPC ........... *H04W 12/084* (2021.01); *H04W 4/50* (2018.02); *H04W 4/80* (2018.02); *H04W 8/005* (2013.01);
(Continued)

(58) Field of Classification Search
CPC .......... H04W 4/30; H04W 4/38; H04W 4/12; H04W 4/14; H04W 4/18; H04W 4/50–80
See application file for complete search history.

(56) References Cited

U.S. PATENT DOCUMENTS

2012/0155276 A1* 6/2012 Vasseur ................. H04W 40/24
370/237
2013/0066703 A1* 3/2013 Razy ................. G06Q 30/0601
705/14.39

(Continued)

FOREIGN PATENT DOCUMENTS

WO 2017/108996 6/2017

OTHER PUBLICATIONS

International Preliminary Report on Patentability and Written Opinion issued Jul. 6, 2023 in International Application No. PCT/US2021/051201.

(Continued)

*Primary Examiner* — San Htun
(74) *Attorney, Agent, or Firm* — Wenderoth, Lind & Ponack, L.L.P.

(57) ABSTRACT

A multi-modal portal system provides an authorization prior to establishing a visual interface connection between a support user or caller and a client user or receiving party. Once the caller is authorized, the caller is permitted to drop-in such that a visual interface connection is established with the receiving party. The authorization can be based on a profile configuration that indicates whether the caller has the credentials required for the visual interface. The authorization can require that a notification be sent to a trusted user or primary contact or the caller can be associated with a profile configuration that allows for a pre-authorization without requiring the notification. Also, security is enhanced by validating network devices and providing resiliency in data paths between network devices and data aggregators.

20 Claims, 16 Drawing Sheets

(51) Int. Cl.
*H04W 4/80* (2018.01)
*H04W 8/00* (2009.01)
*H04W 12/00* (2021.01)
*H04W 12/50* (2021.01)
*H04W 12/60* (2021.01)
*H04W 12/69* (2021.01)
*H04W 68/00* (2009.01)
*H04W 84/08* (2009.01)
*H04W 84/18* (2009.01)
*H04W 40/32* (2009.01)

(52) U.S. Cl.
CPC ......... *H04W 12/009* (2019.01); *H04W 12/50* (2021.01); *H04W 12/66* (2021.01); *H04W 12/69* (2021.01); *H04W 68/005* (2013.01); *H04W 84/08* (2013.01); *H04W 40/32* (2013.01)

(56) References Cited

U.S. PATENT DOCUMENTS

| | | | |
|---|---|---|---|
| 2016/0081127 A1* | 3/2016 | Lee | H04W 12/06 |
| | | | 709/228 |
| 2016/0081134 A1* | 3/2016 | Chow | G06F 16/24578 |
| | | | 455/419 |
| 2016/0234312 A1 | 8/2016 | Vasamsetti et al. | |
| 2017/0006499 A1* | 1/2017 | Hampel | H04W 28/10 |
| 2017/0171314 A1* | 6/2017 | Britt | G06Q 20/308 |
| 2019/0311721 A1* | 10/2019 | Edwards | G10L 17/06 |
| 2020/0022054 A1* | 1/2020 | Hong | H04W 36/0085 |

OTHER PUBLICATIONS

International Search Report and the Written Opinion of the International Searching Authority dated Jan. 4, 2022 in International (PCT) Application No. PCT/US2021/051201.

* cited by examiner

| User Identifier 260 | | | | | |
|---|---|---|---|---|---|
| User Profile 502 | Profile Description 504 | Access Parameters 506 | Device Identifier 508 | Encrypted Credential 510 | Pre-Auth. Access 512 |

FIG. 5A

| User Identifier 260 | | | | | | | | |
|---|---|---|---|---|---|---|---|---|
| User Profile 502 | Profile Description 504 | Access Parameters 506 | | | | | | |
| | | Video Call | Camera Data | Diagnostic Data | Sensor Data | Activity Data | Protected Data | Pre-Auth. |
| Primary Contact | Family Friend Guardian | Yes | Yes | No | Yes | Yes | No | Yes |
| Caregiver | Personal Staff/Nurse | Yes | Yes | Yes | Yes | Yes | No | 512 |
| Healthcare Prof. | Doctor(s) | Yes | Yes | Yes | Yes | Yes | Yes | Yes |
| Coordinator | Care Admin. | Yes | No | No | Yes | No | No | No |
| Personal Services | General Staff | No | No | No | No | No | No | No |
| Auth. Consent Provider | Super User(s)/ Registered Service | Yes | Yes | Yes | Yes | Yes | Yes | Yes |

FIG. 5B

| User Identifier 260 | | | |
|---|---|---|---|
| User Profile 502 | Device Identifier 508 | Encrypted Credentials 510 | Pre-Auth. Access 512 |
| Primary Contact | <Device Name> | <...> | <Auth. Code> |
| Caregiver | Mobile App | <...> | <date>/<time> |
| Healthcare Prof. | Portal | <...> | <Anytime> |
| Coordinator | Mobile App | <...> | <date>/<time? |
| Personal Services | Mobile App | <...> | None |
| Auth. Consent Provider | Mobile App < Device Name> Portal | <...> | <Anytime> |

FIG. 5C

| User Identifier 260 ||||| 
| Task 503 | Task Instruction 505 | Schedule 507 | Video Notification 509 | Additional Video Notification 511 |
| --- | --- | --- | --- | --- |
| Prescription #1 | Dosage #1 | Schedule #1 | Recording A, Recording B | Recording F |
| Prescription #2 | Dosage #2 | Schedule #2 | Recording C, | Recording F |
| Prescription #3 | Dosage #3 | Schedule #3 | Recording D, Recording B | Recording G |
| Prescription #4 | Dosage #4 | Schedule #1 | Recording E | Recording H |
| <New Task> | <New Task Instruction> | <New Scheduled Notification> | <New Video Notification> | <New Additional Video Notification> |

FIG. 5D

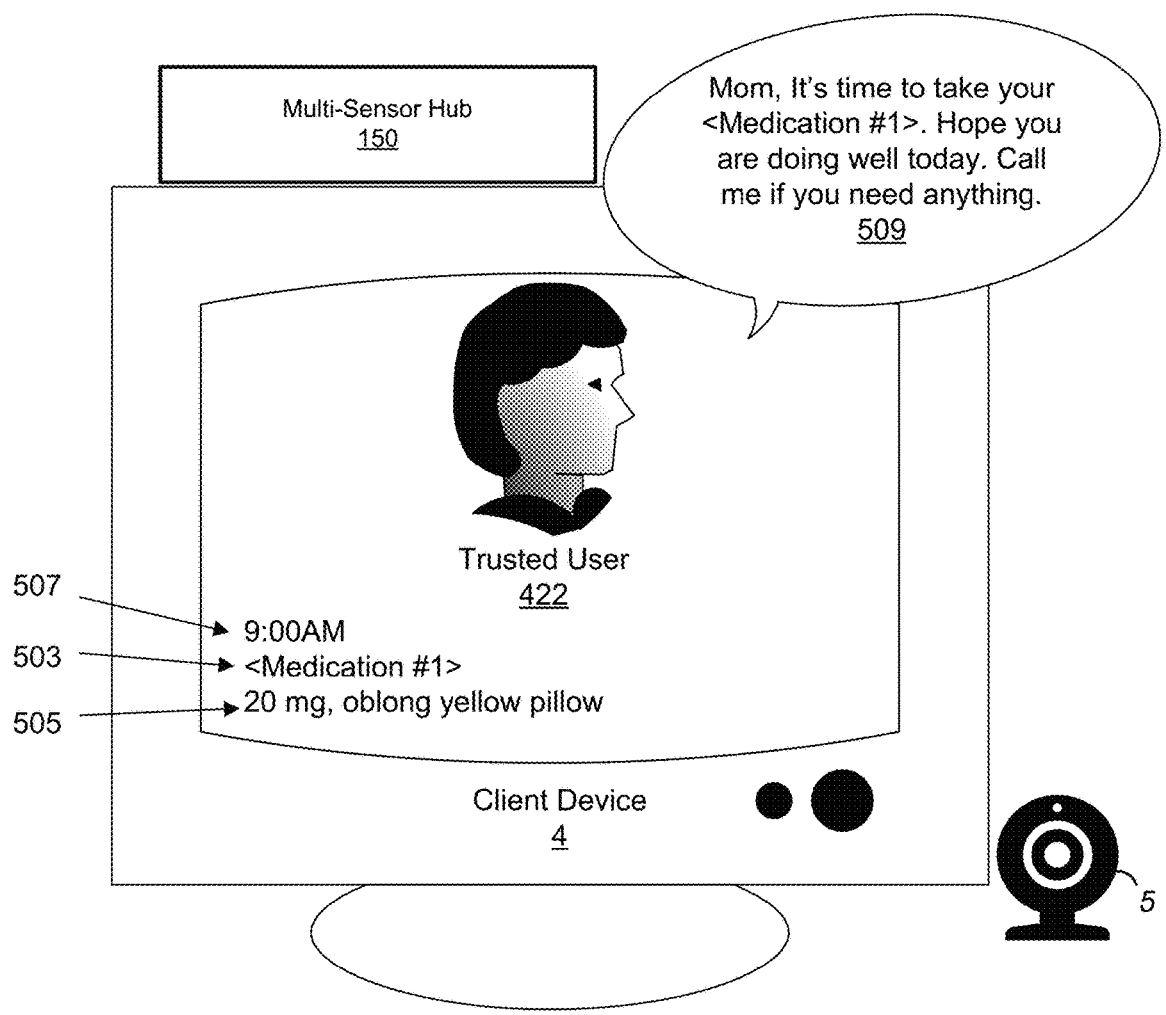

FIG. 13

MULTI-MODAL APPROACH TO A SECURE AND CLOSED SOLUTION FOR PROVIDING SCHEDULED NOTIFICATIONS

BACKGROUND

Wireless in general, and Wi-Fi (wireless fidelity) in particular have become ubiquitous in networking environments such that many devices that previously relied on manual readouts and displays also provide the same information over wireless technologies. This is even more important as there is a concomitant availability of software applications that run on wireless devices (such as mobile phones) that can read the data and provide useful information to the end-user, for example, via a mobile application. For example, as healthcare costs continue to increase, there is an increasing desire with aging adults to stay in place (in home) for extended care services. While there are many individual technologies to address niche problems, given the rapid rise of connectivity technologies and the use of Artificial Intelligence techniques for predictive and analytical methods, these technologies can be confusing and difficult to configure making ubiquitous adoption of a particular technology unlikely. Additionally, services and users are increasingly requiring a visual interface with each other so that a user can be monitored remotely. Thus, there is a need for a more robust, cloud-based approach that accommodates multiple-modes of sensory data to monitor and control access to the sensory data and the user utilizing multiple protocols and redundant data paths while addressing security and privacy concerns associated with the sensory data including validating network devices prior to admission to the network and providing an on-demand visual interface between users.

SUMMARY

Generally, there are many devices in the market that operate or behave as point solutions for specific monitoring of aspects associated with a user. Each solution may have an associated device and an associated application that runs on the associated device. However, these solutions or technologies can require different protocols and solution-specific applications and/or devices. Further, these solutions may not be operable with other solutions or technologies already in use by a user. Accumulating and/or analyzing the data or information from these various solutions or technologies can be daunting and thus not implementable by a user especially when the data is particular sensitive giving rise to security and privacy concerns. According to aspects of the present disclosure there are provided novel solutions for managing and controlling data associated with a user, for example, one or more biometrics or any other sensory data. These novel solutions allow for accommodation of multiple solutions and technologies such that the data associated with the user can be managed and controlled for use by designated or particular individuals to ensure security and privacy of the data. For example, aggregating various data from multiple sensing devices can provide a medical or care staff the information needed to address the well-being of a particular user based on one or more profile configurations that ensure that only authorized or verified users and/or network devices can access the data. In this way, the data is kept secure and privacy is ensured.

Additionally, many services that support a user can benefit from an on-demand visual interface with a user. However, the privacy and security of the user must be safeguarded. For example, as healthcare costs escalate, the need for digital technologies to assist with the aging population is even more important. A novel solution is provided that allows different types of users to visually interface securely and privately with a client user, such as a patient associated with a caregiver network. For example, a video call to a device typically requires that the receiving party accept an incoming call, even if from a known caller, explicitly. But difficulties arise if the receiving party is unable to or cannot access the device to accept the call. Also, if the receiving party requires monitoring on a regular basis using an optical instrument, a camera, for example, requesting consent from the receiving party may not be practical or workable. Thus, there is a need to provide a drop-in or forced video call based on an on-demand authorization.

Further, a user may require specialized care or services. Such specialized care or services can benefit a secure network where network devices are validated prior to admission to the network, redundant data paths, and/or data aggregation from multiple sensing devices using various protocols is provided, as well as from a visual interface that allows for a visual interaction with a user. A visual interface that provides beneficial information as part of a schedule and receives responses from the user to that information can provide an enhanced level of interaction with the user such that in-person communication is not required. Alleviating the need for an in-person communication can reduce costs, expenses and time associated with providing a service to the user, for example, for any of aging-in-place, in-home care, any other service that requires a visual monitor, or any combination thereof.

A novel solution provides for obtaining, consent, authorization, any other verification, or a combination thereof for a network device on the callee/recipient side user to allow a caller user to drop-in or establish a visual interface connection without an express affirmation from the callee user. Authorization can be obtained on-demand or a pre-authorization can be used. The different types of users can visually interface with a callee user via an optical instrument, such as an image capture device, a camera, etc. This visual interface can be monitored and controlled such that an access portal performs an on-demand authorization or an authorization of a request to initiate a visual interface with a client user. In this way, a visual interface can be established with a network device associated with a client user even if the client user is unable to provide feedback or access the network device. Such authorization can also be applied to a novel solution for providing a notification to a user based on a schedule associated with the user where such notifications are provided via a visual interface connection between an authorized device and a client device, such as a multi-sensor hub, associated with the user via a multi-modal portal system. Additionally, such authorization can be applied to admission of a network device to the network, for example, authorization of a data aggregator that collects and sends data associated with a sensing device to a multi-sensor hub using various protocols.

An aspect of the present disclosure provides a multi-sensor hub for admitting a sensing device to a network. The multi-sensor hub comprises a memory storing one or more computer-readable instructions and a processor configured to execute the one or more computer-readable instructions to verify a client user, discover a plurality of multi-sensor devices of the network, wherein at least one multi-sensor device of the plurality of multi-sensor devices is coupled to the multi-sensor hub, derive a relationship of the sensing device to the network, and validate the sensing device, wherein validating the sensing device comprises determining a first multi-sensor device of the plurality of multi-sensor devices as a primary multi-sensor device based on the relationship, associating the sensing device with the primary multi-sensor device via a primary connection, determining a second multi-sensor device of the plurality of multi-sensor devices as a secondary multi-sensor device based on the relationship, associating the sensing device with the secondary multi-sensor device via a secondary connection, and admitting the sensing device to the network.

In an aspect of the present disclosure, the processor is further configured to execute the one or more instructions to detect a failure of the primary multi-sensor device and alert the secondary multi-sensor device of the failure and assign the second connection to be the primary connection.

In an aspect of the present disclosure, the processor is further configured to execute the one or more instructions to assign the secondary multi-sensor device to be the primary multi-sensor device based on the failure and assign the secondary connection to be the primary connection.

In an aspect of the present disclosure, the processor is further configured to execute the one or more instructions to determine a third multi-sensor device of the plurality of multi-sensor devices as the secondary multi-sensor device.

In an aspect of the present disclosure, the processor is further configured to execute the one or more instructions to monitor one or more connectivity factors associated with the plurality of multi-sensor devices, compare the one or more connectivity factors to a corresponding one or more thresholds, and assign the primary multi-sensor device, the secondary multi-sensor device, or both to a different multi-sensor device of the plurality of multi-sensor devices based on the comparison.

In an aspect of the present disclosure, the processor is further configured to execute the one or more instructions to receive one or more messages from at least one multi-sensor device, wherein the one or more messages are indicative of a status of one or more of the plurality of multi-sensor devices and assign the primary multi-sensor device, the secondary multi-sensor device, or both to a different multi-sensor device of the plurality of multi-sensor devices based on the one or more messages.

In an aspect of the present disclosure, the processor is further configured to execute the one or more instructions to maintain an ordered list of the plurality of multi-sensor devices based on one or more connectivity factors associated with each of the plurality of multi-sensor devices.

An aspect of the present disclosure provides a method for admitting a sensing device to a network by a multi-sensor hub. The method comprises verifying a client user, discovering a plurality of multi-sensor devices of the network, wherein at least one multi-sensor device of the plurality of multi-sensor devices is coupled to the multi-sensor hub, deriving a relationship of the sensing device to the network, and validating the sensing device, wherein validating the sensing device comprises determining a first multi-sensor device of the plurality of multi-sensor devices as a primary multi-sensor device based on the relationship, associating the sensing device with the primary multi-sensor device via a primary connection, determining a second multi-sensor device of the plurality of multi-sensor devices as a secondary multi-sensor device based on the relationship, associating the sensing device with the secondary multi-sensor device via a secondary connection, and admitting the sensing device to the network.

In an aspect of the present disclosure, the method further comprises detecting a failure of the primary multi-sensor device and alerting the secondary multi-sensor device of the failure.

In an aspect of the present disclosure, the method further comprises assigning the secondary multi-sensor device to be the primary multi-sensor device based on the failure and assigning the secondary connection to be the primary connection.

In an aspect of the present disclosure, the method further comprises determining a third multi-sensor device of the plurality of multi-sensor devices as the secondary multi-sensor device.

In an aspect of the present disclosure, the method further comprises monitoring one or more connectivity factors associated with the plurality of multi-sensor devices, comparing the one or more connectivity factors to a corresponding one or more thresholds, and assigning the primary multi-sensor device, the secondary multi-sensor device, or both to a different multi-sensor device of the plurality of multi-sensor devices based on the comparison.

In an aspect of the present disclosure, the method further comprises receiving one or more messages from at least one multi-sensor device, wherein the one or more messages are indicative of a status of one or more of the plurality of multi-sensor devices and assigning the primary multi-sensor device, the secondary multi-sensor device, or both to a different multi-sensor device of the plurality of multi-sensor devices based on the one or more messages.

In an aspect of the present disclosure, the method further comprises maintaining an ordered list of the plurality of multi-sensor devices based on one or more connectivity factors associated with each of the plurality of multi-sensor devices.

An aspect of the present disclosure provides a non-transitory computer-readable medium of a multi-modal portal system storing one or more instructions for admitting a sensing device to a network. The one or more instructions when executed by a processor of the multi-sensor hub, cause the multi-sensor hub to perform one or more operations including the steps of the methods described above.

Thus, according to various aspects of the present disclosure described herein, it is possible to manage and control the access to user data, for example, user data received from one or more sensing devices and to provide an on-demand consent response to a visual interface request. The novel solution(s) provide a multi-modal portal system that aggregates information, user data from one or more sensing devices, for use by one or more individuals or users according to an associated profile configuration that includes a user profile associated with one or more access parameters that define the limits to the access, for example, the type of data accessible by a type of user including whether any particular user is authorized to establish a visual interface with a client user. In this way, individuals and/or network devices can obtain necessary information associated with a particular user, for example, a patient or client. Controlling access to the user's data or an optical instrument associated with a client user based on a user profile allows for the management of the user's data from various resources or network devices while preventing unauthorized access to the user's data, such as a visual communication with the client user. For example, certain caregivers, those associated with home care services, may only require a certain level of user data or authorization to access an optical instrument while other caregivers, such as doctors, may require that all user data be accessible including, for example, an on-demand visual interface with the client user via the optical instrument. The user data can be aggregated and made accessible to all the individuals or users associated with a particular user to provide an enhanced QoE for a user while safeguarding privacy and ensuring security. Providing on-demand a visual interface allows a caregiver (the caller), for example, to have a visual interaction with a client user (the callee) without requiring the client user to access or provide consent/authorization to the visual interaction. Rather, access and authorization are provided by the one or more novel aspects of the present disclosure based on a profile configuration associated with the client user. Additionally, this visual interface can provide a notification to the client user based on a scheduled associated with the profile configuration of the user. Further, redundant data paths can be created for network devices that utilize various protocols once the network devices have been authorized and admitted to the network. The data collected from the data aggregators via the redundant data paths can be correlated. The data paths can also be altered to provide resiliency in data transmission and an enhanced network experience.

BRIEF DESCRIPTION OF DRAWINGS

In the drawings, like reference numbers generally indicate identical, functionally similar, and/or structurally similar elements.

FIGS. 5A, 5B, 5C, and 5D are exemplary aspects of a profile configuration for a multi-modal portal system, according to one or more aspects of the present disclosure;

FIG. 13 is an illustration of an example notification to a client user, according to one or more aspects of the present disclosure;

DETAILED DESCRIPTION

The following detailed description is made with reference to the accompanying drawings and is provided to assist in a comprehensive understanding of various example embodiments of the present disclosure. The following description includes various details to assist in that understanding, but these are to be regarded merely as examples and not for the purpose of limiting the present disclosure as defined by the appended claims and their equivalents. The words and phrases used in the following description are merely used to enable a clear and consistent understanding of the present disclosure. In addition, descriptions of well-known structures, functions, and configurations may have been omitted for clarity and conciseness. Those of ordinary skill in the art will recognize that various changes and modifications of the examples described herein can be made without departing from the spirit and scope of the present disclosure.

Figure 1:
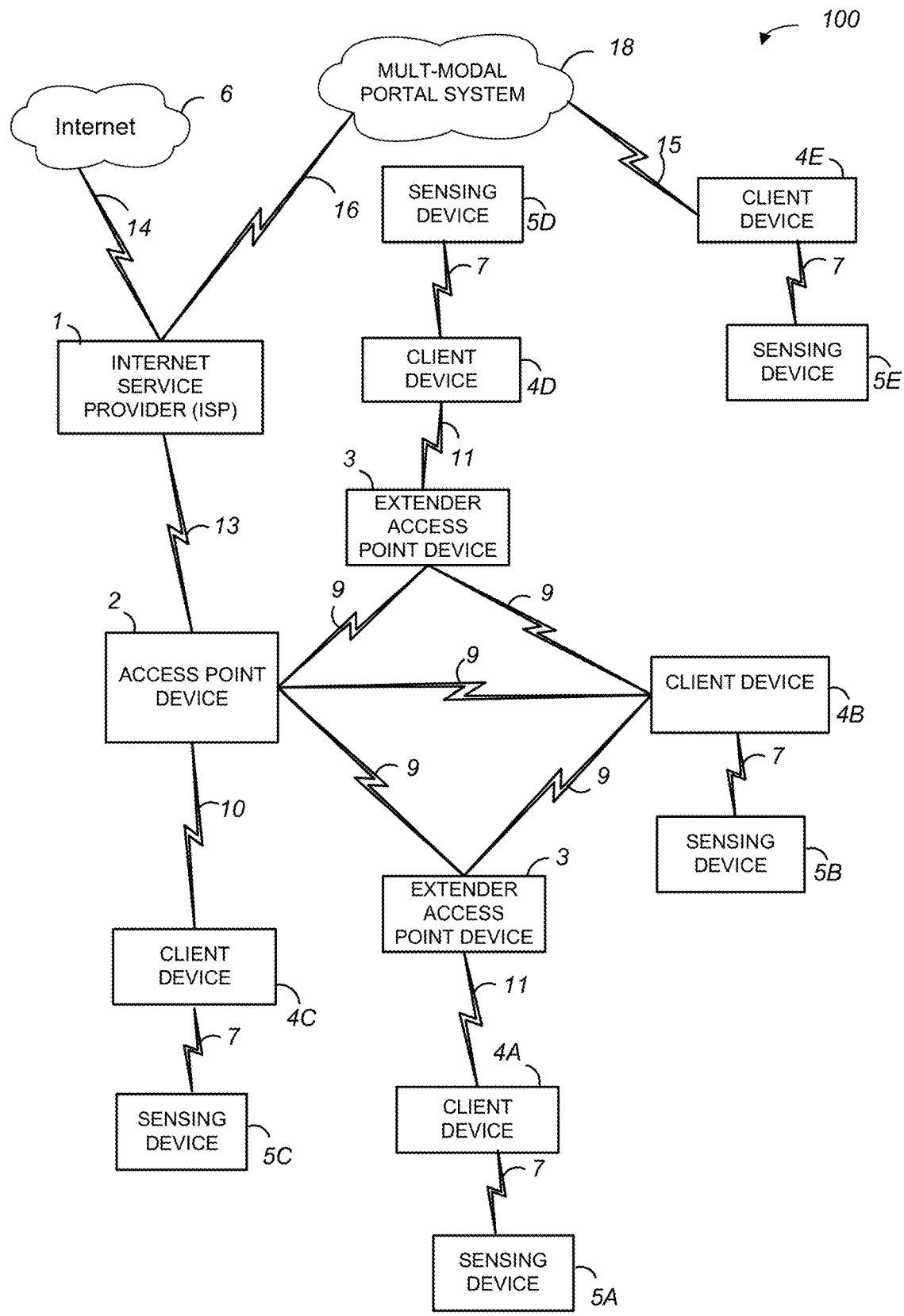
FIG. 1 is a schematic diagram of a network environment, according to one or more aspects of the present disclosure.

FIG. 1 is a schematic diagram of a network environment 100, according to one or more aspects of the present disclosure. For example, a secure, multi-modal, multi-protocol monitoring and communication network environment can provide for aggregation of user data from multiple network devices and/or sources. An example network environment can be related to a caregiving network for a user (a patient) such that one or more aspects associated with the user (for example, biometric data, a visual interface, etc.) can be aggregated and/or monitored from multiple network devices capable of sensing the one or more aspects. For example, any one or more users, such as in a trusted support network, can establish a visual interface with a particular user based on an authorization for the visual interface. Access to the aggregated and/or monitored data, including the visual interface, can be controlled based on one or more profile configurations as discussed with reference to FIGS. 5A-5D.

It should be appreciated that various example embodiments of inventive concepts disclosed herein are not limited to specific numbers or combinations of devices, and there may be one or multiple of some of the aforementioned electronic apparatuses in the network environment, which may itself consist of multiple communication networks and various known or future developed wireless connectivity technologies, protocols, devices, and the like.

As shown in FIG. 1, the main elements of the network environment 100 include a network comprising an access point device 2 connected to a network resource such as any of the Internet 6, a multi-modal portal system 18, any other cloud storage/repository, or any combination thereof via an Internet Service Provider (ISP) 1 and also connected to different wireless devices or network devices such as one or more wireless extender access point devices 3, one or more client devices 4A-4E (collectively referred to as client device(s) 4), and one or more sensing devices 5A-5E (collectively referred to as sensing device(s) 5). The network environment 100 shown in FIG. 1 includes wireless network devices (e.g., extender access point devices 3 and client devices 4) that may be connected in one or more wireless networks (e.g., private, guest, iControl, backhaul network, or Internet of things (IoT) network) within the network environment 100. Additionally, there could be some overlap between wireless devices (e.g., extender access point devices 3 and client devices 4) in the different networks. That is, one or more network or wireless devices could be located in more than one network. For example, the extender access point devices 3 could be located both in a private network for providing content and information to a client device 4 and also included in a backhaul network or an iControl network.

Starting from the top of FIG. 1, the ISP 1 can be, for example, a content provider or any computer for connecting the access point device 2 to a network resource, such as Internet 6 and multi-modal portal system 18. For example, Internet 6 can be a cloud-based service that provides access to a cloud-based repository accessible via ISP 1 where the cloud-based repository comprises information associated with or an access requested by any one or more network devices of the network environment 100. The multi-modal portal system 18 can provide monitoring, aggregation and/or controlling of data associated with a user in the network environment 100, such as data collected by one or more sensing devices 5. In one or more embodiments, the multi-modal portal system 18 can communicate with any one or more external repositories of Internet 6 via ISP 1 or internal repositories, such as a notification repository. In one or more embodiments, any of the sensing devices 5 can be directly or indirectly coupled to the multi-modal portal system 18. The connection 14 between the Internet 6 and the ISP 1, the connection 16 between the multi-modal portal system 18 and the ISP 1, the connection 15 between the multi-modal portal system 18 and the client device 5E, and the connection 13 between the ISP 1 and the access point device 2 can be implemented using a wide area network (WAN), a virtual private network (VPN), metropolitan area networks (MANs), system area networks (SANs), a data over cable service interface specification (DOCSIS) network, a fiber optics network (e.g., FTTH (fiber to the home) or FTTX (fiber to the x), or hybrid fiber-coaxial (HFC)), a digital subscriber line (DSL), a public switched data network (PSDN), a global Telex network, or a 2G, 3G, 4G, 5G, or 6G network, for example.

Any of the connections 13, 14, 15, 16, or any combination thereof (collectively referred to as network connections or connections) can further include as some portion thereof a broadband mobile phone network connection, an optical network connection, or other similar connections. For example, any of the network connections can also be implemented using a fixed wireless connection that operates in accordance with, but is not limited to, 3rd Generation Partnership Project (3GPP) Long Term Evolution (LTE), 5G, or 6G protocols. It is also contemplated by the present disclosure that any of the network connections are capable of providing connections between a network device and a WAN, a LAN, a VPN, MANs, PANs, WLANs, SANs, a DOCSIS network, a fiber optics network (e.g., FTTH, FTTX, or HFC), a PSDN, a global Telex network, or a 2G, 3G, 4G, 5G or 6G network, for example.

The access point device 2 can be, for example, an access point and/or a hardware electronic device that may be a combination modem and gateway that combines the functions of a modem, an access point (AP), and/or a router for providing content received from the ISP 1 to one or more network devices (e.g., wireless extender access point devices 3 and client devices 4) in the network environment 100, or any combination thereof. It is also contemplated by the present disclosure that the access point device 2 can include the function of, but is not limited to, a universal plug and play (UPnP) simple network management protocol (SNMP), an Internet Protocol/Quadrature Amplitude Modulator (IP/QAM) set-top box (STB) or smart media device (SMD) that is capable of decoding audio/video content, and playing over-the-top (OTT) or multiple system operator (MSO) provided content. The access point device 2 may also be referred to as a residential gateway, a home network gateway, or a wireless access point (AP).

The connection 9 between the access point device 2 and the wireless extender access point devices 3, and client device 4B can be implemented using a wireless connection in accordance with any IEEE 802.11 Wi-Fi protocols, Bluetooth protocols, Bluetooth Low Energy (BLE), or other short range protocols that operate in accordance with a wireless technology standard for exchanging data over short distances using any licensed or unlicensed band such as the citizens broadband radio service (CBRS) band, 2.4 GHz bands, 5 GHz bands, 6 GHz bands, or 60 GHz bands. Additionally, the connection 9 can be implemented using a wireless connection that operates in accordance with, but is not limited to, RF4CE protocol, ZigBee protocol, Z-Wave protocol, or IEEE 802.15.4 protocol. It is also contemplated by the present disclosure that the connection 9 can include connections to a media over coax (MoCA) network. One or more of the connections 9 can also be a wired Ethernet connection. Any one or more of connections 9 can carry information on any of one or more channels that are available for use.

The extender access point devices 3 can be, for example, wireless hardware electronic devices such as access points (APs), extenders, repeaters, etc. used to extend the wireless network by receiving the signals transmitted by the access point device 2 and rebroadcasting the signals to, for example, client devices 4, which may be out of range of the access point device 2. The extender access point devices 3 can also receive signals from the client devices 4 and rebroadcast the signals to the access point device 2, or other client devices 4.

The connection 11 between the extender access point devices 3 and the client devices 4A and 4D are implemented through a wireless connection that operates in accordance with any IEEE 802.11 Wi-Fi protocols, Bluetooth protocols, BLE, or other short range protocols that operate in accordance with a wireless technology standard for exchanging data over short distances using any licensed or unlicensed band such as the CBRS band, 2.4 GHz bands, 5 GHz bands, 6 GHz bands, or 60 GHz bands. Additionally, the connection 11 can be implemented using a wireless connection that operates in accordance with, but is not limited to, RF4CE protocol, ZigBee protocol, Z-Wave protocol, or IEEE 802.15.4 protocol. Also, one or more of the connections 11 can be a wired Ethernet connection. Any one or more connections 11 can carry information on any one or more channels that are available for use.

The client devices 4 can be, for example, hand-held computing devices, personal computers, electronic tablets, mobile phones, smart phones, smart speakers, Internet-of-Things (IoT) devices, iControl devices, portable music players with smart capabilities capable of connecting to the Internet, cellular networks, and interconnecting with other devices via Wi-Fi and Bluetooth, or other wireless hand-held consumer electronic devices capable of executing and displaying content received through the access point device 2. Additionally, the client devices 4 can be a television (TV), an IP/QAM set-top box (STB) or a streaming media decoder (SMD) that is capable of decoding audio/video content, and playing over OTT or MSO provided content received through the access point device 2. Further, a client device 4 can be a network device that requires configuration by the access point device 2. In one or more embodiments, the client devices 4 can comprise any network device associated with a user for interacting with any type of one or more sensing devices 5. For example, the client device 4 can interact with a plurality of sensing devices 5 where each sensing device 5 senses one or more aspects associated with a user or an environment. In one or more embodiments, one or more sensing devices 5 are included within or local to (built-in) the client device 4.

One or more sensing devices 5 can connect to one or more client devices 4, for example, via a connection 7. Connection 7 can utilize any one or more protocols discussed above with respect to connection 9. Any of the one or more sensing devices 5 can comprise or be coupled to an optical instrument (such as a camera, an image capture device, or any other visual user interface device, any device for capturing an image, a video, a multi-media video, or any other type of data, or a combination thereof), a biometric sensor, a biometric tracker or sensor, ambient temperature sensor, a light sensor, a humidity sensor, a motion detector (such as, an infrared motion sensor or Wi-Fi motion sensor), a facial recognition system, a medical diagnostic sensor (such as, a pulse oximeter or any other oxygen saturation sensing system, a blood pressure monitor, a temperature sensor, a glucose monitor, etc.), a voice recognition system, a microphone (such as, a far field voice (FFV) microphone) or other voice capture system, any other sensing device, or a combination thereof.

The connection 10 between the access point device 2 and the client device 4 is implemented through a wireless connection that operates in accordance with, but is not limited to, any IEEE 802.11 protocols. Additionally, the connection 10 between the access point device 2 and the client device 4C can also be implemented through a WAN, a LAN, a VPN, MANs, PANs, WLANs, SANs, a DOCSIS network, a fiber optics network (e.g., FTTH, FTTX, or HFC), a PSDN, a global Telex network, or a 2G, 3G, 4G, 5G or 6G network, for example.

The connection 10 can also be implemented using a wireless connection in accordance with Bluetooth protocols, BLE, or other short range protocols that operate in accordance with a wireless technology standard for exchanging data over short distances using any licensed or unlicensed band such as the CBRS band, 2.4 GHz bands, 5 GHz bands, 6 GHz bands or 60 GHz bands. One or more of the connections 10 can also be a wired Ethernet connection. In one or more embodiments, any one or more client devices 4 utilize a protocol different than that of the access point device 2.

It is contemplated by the present disclosure that the multi-modal portal system 18, the access point device 2, the extender access point devices 3, and the client devices 4 include electronic components or electronic computing devices operable to receive, transmit, process, store, and/or manage data and information associated with the network environment 100, which encompasses any suitable processing device adapted to perform computing tasks consistent with the execution of computer-readable instructions stored in a memory or a computer-readable recording medium (e.g., a non-transitory computer-readable medium). In one or more embodiments, the network environment 100 can be a self-organizing hybrid IoT hub mesh topology for resilient static and mobile sensor data collection. For example, any one or more sensing devices 5 can collect data and send the data via a client device 4 (such as a data aggregator) via a plurality of data paths or connections.

Further, any, all, or some of the computing components in the multi-modal portal system 18, access point device 2, the extender access point devices 3, and the client devices 4 may be adapted to execute any operating system, including Linux, UNIX, Windows, MacOS, DOS, and ChromOS as well as virtual machines adapted to virtualize execution of a particular operating system, including customized and proprietary operating systems. The multi-modal portal system 18, the access point device 2, the extender access point devices 3, and the client devices 4 are further equipped with components to facilitate communication with other computing devices or network devices over the one or more network connections to local and wide area networks, wireless and wired networks, public and private networks, and any other communication network enabling communication in the network environment 100.

Figure 15:
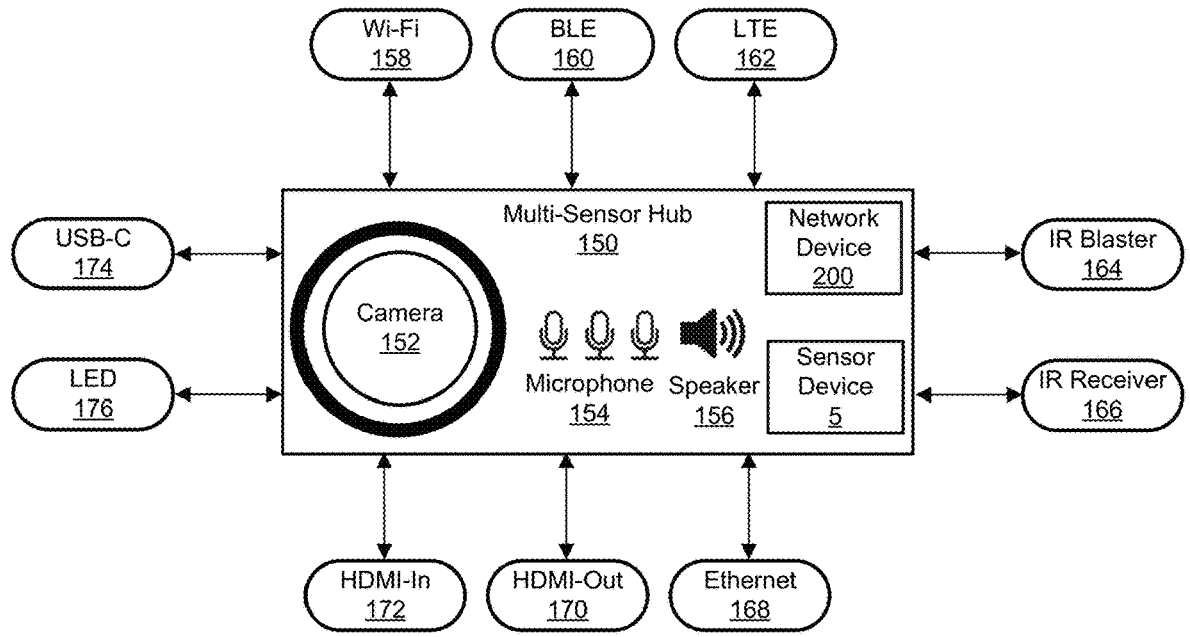
FIG. 15 is an exemplary multi-sensor hub, according to one or more aspects of the present disclosure.
Figure 14:
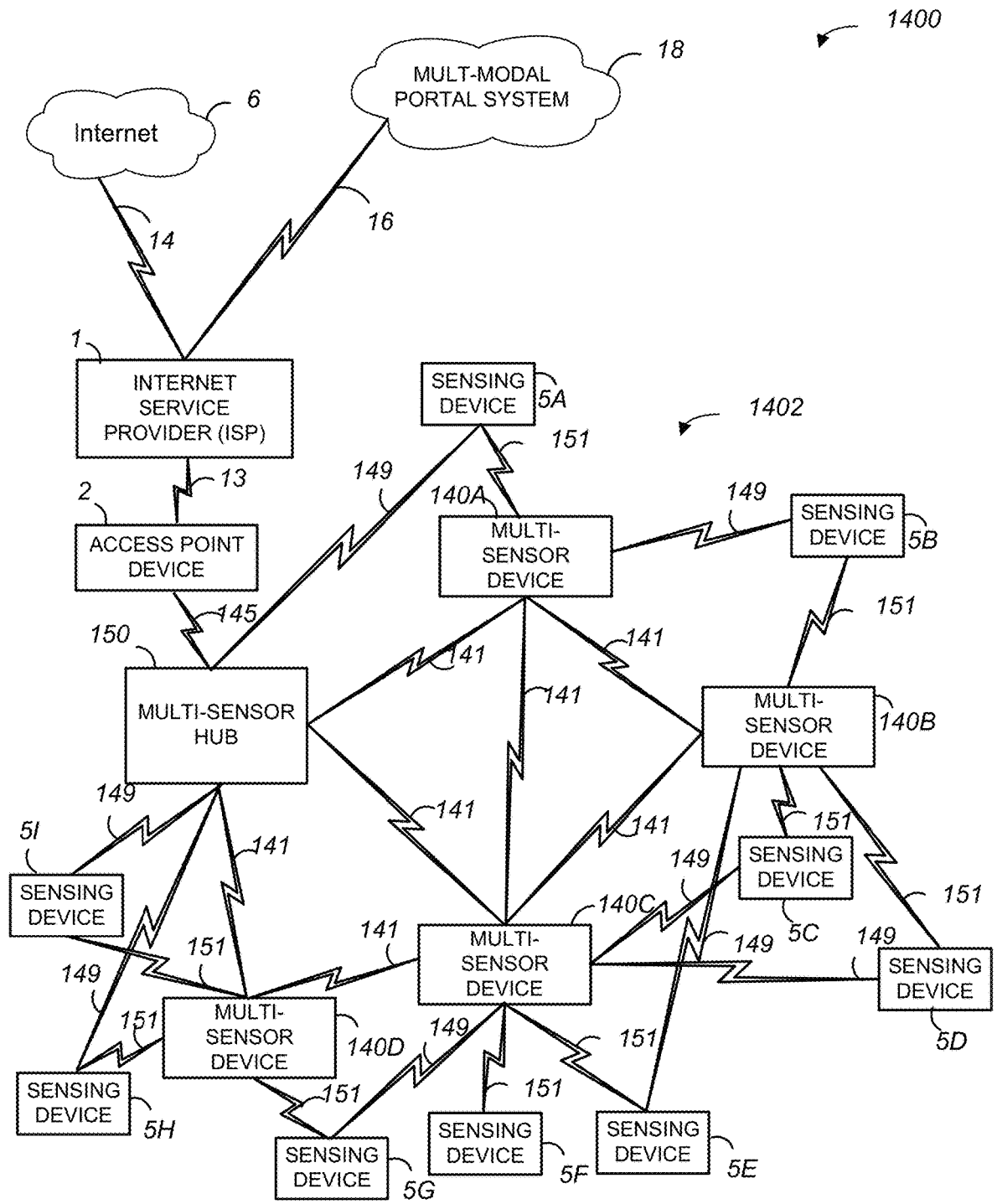
FIG. 14 is a schematic diagram of a network environment that includes a hybrid topology with resiliency across multiple sensor data paths, according to one or more aspects of the present disclosure.

In one or more embodiments, a network environment 100 could be augmented, altered or replaced with a network environment 1400 as illustrated in FIG. 14. FIG. 14 illustrates a schematic diagram of a network environment 1400 that includes a hybrid topology that comprises various types of sensing devices 5 that utilize various communications protocols, across multiple or redundant sensor data paths, according to one or more aspects of the present disclosure. The access point device 2 can be connected via a connection 145 to a multi-sensor hub 150. In one or more embodiments, the multi-sensor hub 150 is connected to the access point device 2 via an extender access point device 3. The connection 145 can be any type of wireless or wired connection as discussed with reference to FIG. 1. The multi-sensor hub 150 can comprise one or more components, for example, as illustrated in FIG. 15. The multi-sensor hub 150 can send or transmit data received from the one or more multi-sensor devices 140 upstream to a cloud resource, such as a multi-modal portal system 18, for analysis or further processing.

FIG. 15 illustrates a multi-sensor hub 150, according to one or more aspects of the present disclosure. The multi-sensor hub 150 can include an optical instrument or image capture device (such as a camera 152 or any other device that can obtain one or more visuals of a client user), an audio input device (such as a microphone 154, a microphone array, a far field voice (FFV) solution, etc.), an audio output device (such as a speaker 156), a sensing device 5, and a network device 200. In one or more embodiments, any one or more components of the multi-sensor hub 150 can be included within or connected to the multi-sensor hub 150. The multi-sensor hub 150 can include any of one or more ports or receivers, for example, a Wi-Fi (such as a Wi-Fi5 (dual-band simultaneous (DBS))) port 158, a BLE port 160, an LTE port 162, an infrared (IR) blaster port 164, and IR receiver port (166), an Ethernet port 168, an HDMI-Out port 170, an HDMI-In port 172, an external power supply (such as a universal serial bus type-C (USB-C), an LED output 176, or any combination thereof. The sensing device 5 can include any one or more types of sensors such as any of a power sensor, a temperature sensor, a light sensor, a humidity sensor, a motion sensor, a biometric sensor (such as a blood pressure monitor, oxygen saturation meter, pulse meter, etc.), any other type of sensor, or any combination thereof. In one or more embodiments, the sensing device 5 can be an IoT device. The network device 200 can include software, for example, as discussed with respect to FIGS. 11 and 12, to receive any of a video notification, for example, as discussed with reference to FIG. 5D, an image (for example of a client user) via camera 152, any data associated with one or more sensor devices 5, microphone 154, speaker 156, any other element, or combination thereof. The video notification can include data for display on a display device associated with the multi-sensor hub 150, for example, any of a television, a monitor, a client device 4 with display functionality connected to and/or part of the multi-sensor hub 150, a user interface (such as user interface 20 discussed with reference to FIG. 2), or any combination thereof.

Turning back to FIG. 14, the multi-sensor hub 150 can be connected to one or more sensing devices 5 (for example, any of sensing devices 5A-5I), one or more multi-sensor devices 140 (for example, any of multi-sensor devices 140A-D), and any combination thereof. For example, for remote well-being monitoring, the one or more multi-sensor devices can collect data from a variety of sources, such as one or more sensing devices 5, with different capabilities. In additional to functional differences, the one or more sensing devices 5 can have differences in the protocol or method of communication to one or more multi-sensor devices 140. The one or more multi-sensor devices 140 can be data aggregators that collect data from the one or more sensing devices 5 and send the collected data to the multi-sensor hub 150. To provide coverage for the various sensing devices 5 distributed at or about a premises (such as a network 1402), a plurality of multi-sensor devices 140 can be distributed within range of the one or more sensing devices 5 so as to provide resiliency or redundancy in the data aggregation of data collected or received from the one or more sensing devices 5. The multi-sensor device 140 can comprise any one or more elements of a network device 200 but with limited connectivity functionality, such as short range wireless protocol functionality. For example, the multi-sensor device 140 does not require Wi-Fi connectivity but rather can communicate with the multi-sensor hub 150 using any one or more short range wireless protocols. A multi-sensor device 140 can include any of a BLE radio, a ZigBee radio, a LoRa radio, any other short range connectivity technology, or any combination thereof for communication to any of one or more sensing devices 5, one or more multi-sensor devices 140, the multi-sensor hub 150, or any combination thereof. The multi-sensor device 140 can also include any of a sensor (such as a sensing device 5), an external power source, associated connectivity software, such as BLE mesh networking software, or any combination thereof. For example, the multi-sensor hub 150 can connect to one or more multi-sensor devices 140 via a Bluetooth mesh connection 141. The multi-sensor hub 150 and/or the one or more multi-sensor devices 140 can connect to one or more sensing devices 5 via a primary connection 151, a secondary connection 149 or both so as to establish a resilient hybrid topology network. In one or more embodiments, the one or more multi-sensor devices 140 and the multi-sensor hub 150 along with associated connections constitute a mesh topology, for example, as discussed with reference to FIG. 3.

As an example, a multi-sensor hub 150 can connect to a sensing device 5A via a secondary connection 149, a multi-sensor device 140A via a connection 141, a multi-sensor device 140C via a connection 141, a multi-sensor device 140D via a connection 141, a sensing device 5H via a secondary connection 149, and a sensing device 5I via a secondary connection 149. The multi-sensor device 140A can also connect to the sensing device 5A via a primary connection 151, a sensing device 5B via a secondary connection 149, a multi-sensor device 140B via a connection 141 and a multi-sensor device 140C via a connection 141. The multi-sensor device 140B can also connect to the sensing device 5B via a primary connection 151, a sensing device 5D via a primary connection 151, a sensing device 5C via a primary connection 151, and a sensing device 5E via a secondary connection 149. The multi-sensor device 140C can also connect to the sensing device 5E via a primary connection 151, a sensing device 5F via a primary connection 151, a sensing device 5G via a secondary connection 149, and the multi-sensor device 140D via a connection 141. The multi-sensor device 140D can also connect to the sensing device 5G via a primary connection 151, the sensing device 5H via a primary connection 151, and the sensing device 5I via the primary connection 151. In one or more embodiments, the primary connection 151, the secondary connection 149, or both can be any type of short range connection.

A multi-sensor device 140 can be distributed throughout a network 1402 associated with the network environment 1400, for example, any of a home, a care provider, an assisted living facility, any other environment that requires receiving or aggregating data from various sensing device 5, or any combination thereof. In one or more embodiments, the primary connection 151 provides a sensor data path for data associated with a sensing device 5. In one or more embodiments, the secondary connection 149 provides a redundant or back-up sensor data path for data associated with the sensing device 5. For example, if a multi-sensor device 140 experiences a failure, becomes overloaded, or otherwise does not function or operate properly or as expected the sensing device 5 can be instructed to switch to the secondary connection 149 to a primary connection 151 and to establish a new secondary connection 149 with a different multi-sensor device 140 or to only maintain the new primary connection 151. For example, a sensing device 5B can be instructed to disconnect the primary connection 151 to the multi-sensor device 140B and/or switch to the secondary connection 149 to the multi-sensor device 140A as a new primary connection 151. For example, the multi-sensor hub 150 can determine that the path associated with the multi-sensor device 140B experiences more latency due to the multiple connection points than the path associated with the multi-sensor device 140A which has a direct connection 141 to the multi-sensor hub 150 such that the secondary and primary paths should be switched.

In one or more embodiments the network 1402 can comprise a Bluetooth mesh topology that allows for resilience in terms of transmission of data collected or aggregated from the one or more sensing device 5 and/or the one or more multi-sensor devices 140 and sent to the access point device 2 via the multi-sensor hub 150. In one or more embodiments, the topology of network 1402 is not a full mesh topology where every multi-sensor device 140 or data aggregator is able to communicate with every other multi-sensor device 140 or data aggregator but still provides the availability of multiple data paths to the access point device 2 so as to provide resiliency.

Figure 2:
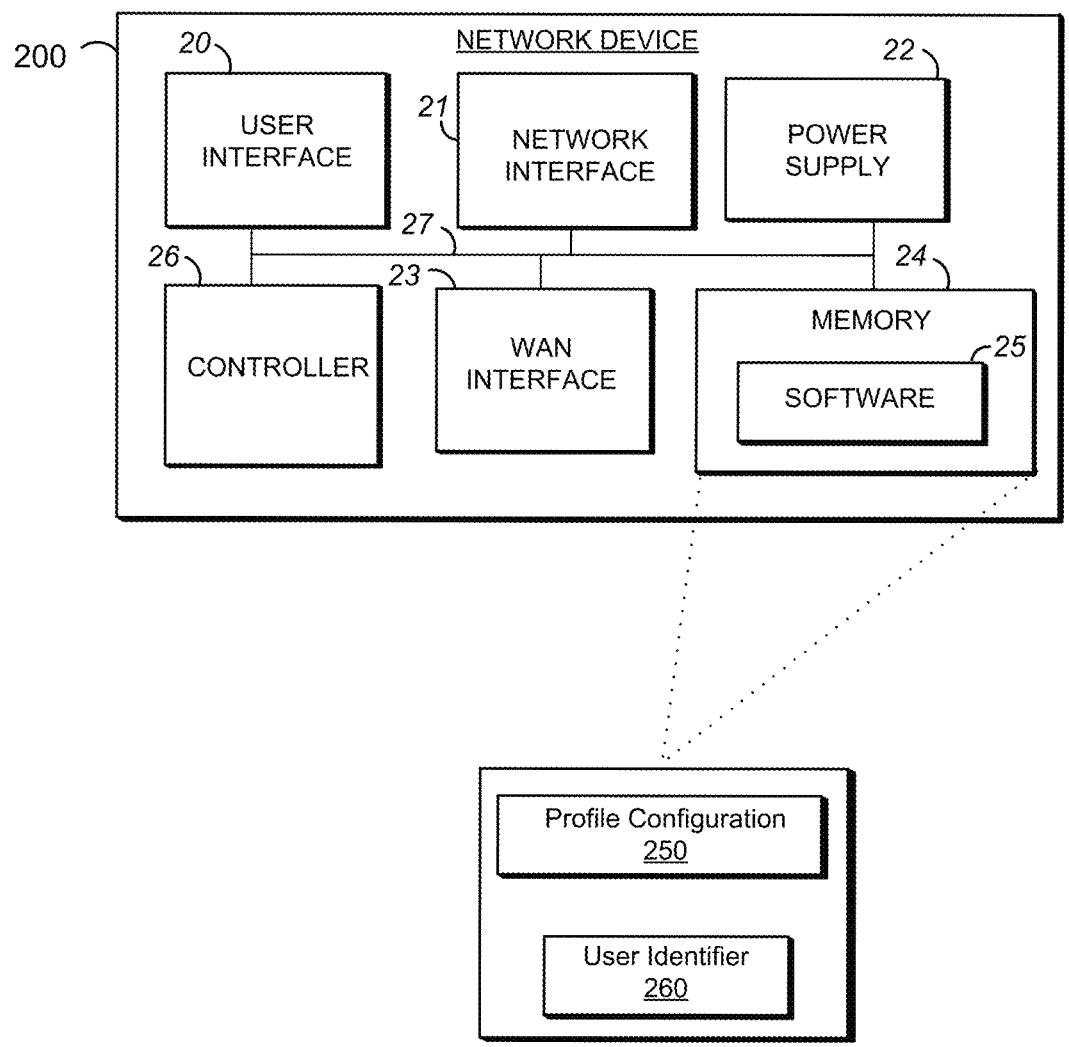
FIG. 2 is a more detailed block diagram illustrating various components of a network device, according to one or more aspects of the present disclosure.

FIG. 2 is a more detailed block diagram illustrating various components of an exemplary network device 200, such as a network device comprising a multi-modal portal system 18, an access point device 2, an extender access point device 3, a client device 4, any other network device, or any combination thereof implemented in the network environment 100 of FIG. 1, according to one or more aspects of the present disclosure.

Now referring to FIG. 2 the network device 200 can be, for example, a computer, a server, any other computer device with smart capabilities capable of connecting to the Internet, cellular networks, and interconnecting with other network devices via Wi-Fi and Bluetooth, or other wireless hand-held consumer electronic device capable of providing management and control of user data, for example, a multi-modal portal system 18, according to one or more aspects of the present disclosure. The network device 200 includes one or more internal components, such as a user interface 20, a network interface 21, a power supply 22, a controller 26, a WAN interface 23, a memory 34, and a bus 27 interconnecting the one or more elements.

The power supply 22 supplies power to the one or more internal components of the network device 200 through the internal bus 27. The power supply 22 can be a self-contained power source such as a battery pack with an interface to be powered through an electrical charger connected to an outlet (e.g., either directly or by way of another device). The power supply 22 can also include a rechargeable battery that can be detached allowing for replacement such as a nickel-cadmium (NiCd), nickel metal hydride (NiMH), a lithium-ion (Li-ion), or a lithium Polymer (Li-pol) battery.

The user interface 20 includes, but is not limited to, push buttons, a keyboard, a keypad, a liquid crystal display (LCD), a thin film transistor (TFT), a light-emitting diode (LED), a high definition (HD) or other similar display device including a display device having touch screen capabilities so as to allow interaction between a user and the network device 200, for example, for a user to enter any one or more profile configurations 250, a user identifier 260, any other information associated with a user or network device, or a combination thereof that are stored in memory 34. The network interface 20 can include, but is not limited to, various network cards, interfaces, and circuitry implemented in software and/or hardware to enable communications with and/or between the multi-modal portal system 18, the access point device 2, an extender access point device 3, and/or a client device 4 using any one or more of the communication protocols in accordance with any one or more connections (e.g., as described with reference to FIG. 1). In one or more embodiments, the user interface 20 enables communications with a sensing device 5, directly or indirectly.

The memory 24 includes a single memory or one or more memories or memory locations that include, but are not limited to, a random access memory (RAM), a dynamic random access memory (DRAM) a memory buffer, a hard drive, a database, an erasable programmable read only memory (EPROM), an electrically erasable programmable read only memory (EEPROM), a read only memory (ROM), a flash memory, logic blocks of a field programmable gate array (FPGA), an optical storage system, a hard disk or any other various layers of memory hierarchy. The memory 24 can be used to store any type of instructions, software, or algorithms including software 25, for example, a multi-modal portal application, for controlling the general function and operations of the network device 200 in accordance with one or more embodiments. In one or more embodiments, memory 24 can store any one or more profile configurations 250 associated with one or more user identifiers 260 so as to provide (for example, by a multi-modal portal application of a multi-modal portal system 18) aggregation, monitoring, and control of user data, such as user data received from one or more sensing devices 5. For example, controlling or establishing a visual interface connection between two network devices, such as between a client device 4E and a client device 4C or between a network device associated with a client user and a network device associated with a trusted user (also referred to as a trusted user device). The controlling the visual interface connection can include providing an authorization to a visual interface request as discussed with reference to FIG. 7. The one or more user identifiers 260 can comprise a unique identifier associated with one or more users, one or more network devices, or both. The one or more user identifiers 260 can be associated with one or more profile configurations 250 which include information associated with one or more profiles of one or more users. The multi-modal portal application can manage and control access to user data associated with the one or more user identifiers 260 based on the one or more profile configurations 250. In one or more embodiments, the profile configuration 250 and/or the user identifier 260 is stored in any type of storage medium local to or remote from the network device 200.

The controller 26 controls the general operations of the network device 200 and includes, but is not limited to, a central processing unit (CPU), a hardware microprocessor, a hardware processor, a multi-core processor, a single core processor, a field programmable gate array (FPGA), a microcontroller, an application specific integrated circuit (ASIC), a digital signal processor (DSP), or other similar processing device capable of executing any type of instructions, algorithms, or software including the software 25 which can include a multi-modal portal application in accordance with one or more embodiments. Communication between the components (e.g., 20-26) of the network device 200 may be established using an internal bus 27.

The network interface 21 can include various network cards, interfaces, and circuitry implemented in software and/or hardware to enable communications with any one or more other network devices, for example, any of a client device 4, ISP 1, any other network device (e.g., as described with reference to FIG. 1), or a combination thereof. The communications can utilize a visual interface connection that allows for a visual interface between two users, for example, a communication that utilizes an optical instrument (such as for a video call or for an image capture). For example, the network interface 21 can include multiple radios or sets of radios (e.g., a 2.4 GHz radio, one or more 5 GHz radios, and/or a 6 GHz radio), which may also be referred to as wireless local area network (WLAN) interfaces. In one or more embodiments, one radio or set of radios (e.g., 5 GHz and/or 6 GHz radio(s)) provides a backhaul connection between the wireless extender access point device 3 and the access point device 2, and optionally other wireless extender access point device(s) 3. In one or more embodiments, the multi-modal portal system 18 is connected to or is part of the access point device 2 such that a backhaul connection is established between the multi-modal portal system 18 and one or more wireless extender access point devices 3. Another radio or set of radios (e.g., 2.4 GHz, 5 GHz, and/or 6 GHz radio(s)) provides a fronthaul connection between the extender access point device 3 and one or more client device(s) 4.

The wide area network (WAN) interface 23 may include various network cards, and circuitry implemented in software and/or hardware to enable communications between the access point device 2 and the ISP 1 using the wired and/or wireless protocols in accordance with connection 13 (e.g., as described with reference to FIG. 1).

Figure 3:
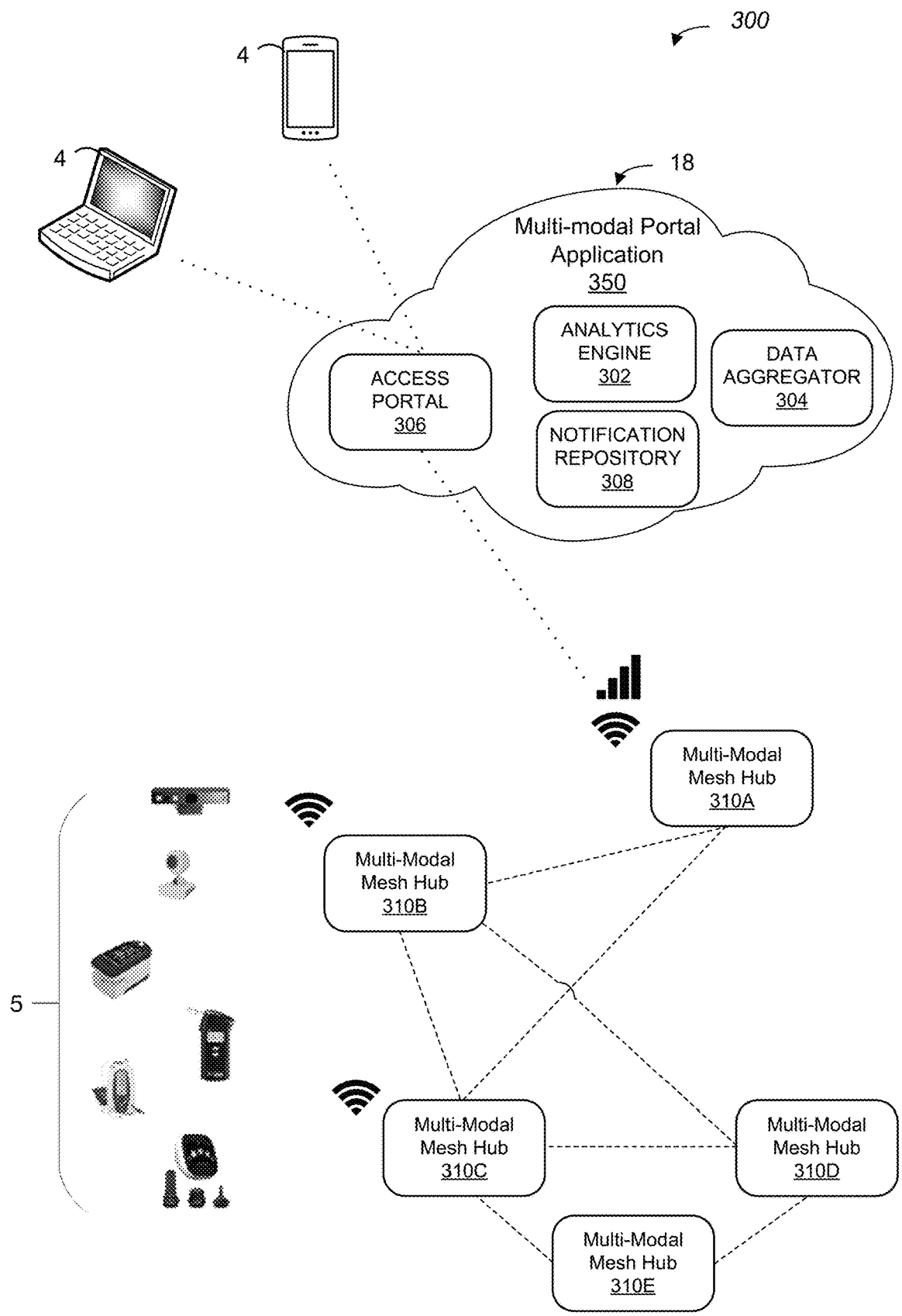
FIG. 3 is an illustration of a multi-modal portal system in a network environment, according to one or more aspects of the present disclosure.

FIG. 3 illustrates a multi-modal portal system 18 in a network environment 300, according to one or more aspects of the present disclosure. The network environment 300 provides an end-to-end closed network for management, control, and access of user data by one or more authorized users, including a visual interface between multiple users. The network environment 300 includes a multi-modal portal system 18, one or more client devices 4, one or more multi-modal mesh hubs 310A, 310B, 310C, 310D, and 310E (collectively referred to as multi-modal mesh hub(s) 310), and one or more sensing devices 5. In one or more embodiments, any of the multi-modal mesh hubs 310 can comprise an IoT hub, a multi-sensor hub 150, or a multi-sensor device 140 that provides an interface to one or more sensing devices 5, including an interface that provides for a visual interface connection. In one or more embodiments, any one or more of the multi-modal mesh hubs 310 can store user data from any of the one or more sensing devices 5, for example, when a connection to the multi-modal portal system 18 is not available.

The multi-modal portal system 18 can be a network device 200 as discussed with reference to FIG. 2. The multi-modal portal system 18 provides a well-defined secure storage, aging, purging and external data transmission with egress points for user data based on explicit authorization with complete audit trail. The multi-modal portal system 18 can comprise a multi-modal portal application 350.

The multi-modal portal application 350 can provide management, control, and access of user data associated with one or more users. The multi-modal portal application 350 provides a secure remote interface to information associated with a user based one or more profile configurations. For example, the multi-modal portal application 350 can comprise an access portal 306, an analytics engine 302, a data aggregator 304, and a notification repository 308. The access portal 306 can provide an interface to one or more client devices 4 connected directly or indirectly to the multi-modal portal system 18 and one or more multi-modal mesh hubs 310. The access portal 302 can comprise any of an application programming interface (API), a webpage, a graphical user interface, any other interface, or a combination thereof. For example, the interface can include a visual interface connection that can be established between any two network devices. Additionally, the access portal 306 can receive one or more requests from one or more requestors, such as from one or more network devices (such as one or more client devices 4, one or more sensing devices 5, or a combination thereof).

The data aggregator 304 can comprise any type of non-transitory computer-readable storage medium as discussed with reference to FIG. 2. The data aggregator 304 can store user data and/or one or more profile configurations 250, the one or more user identifiers 260, or both. The user data and/or the one or more profile configurations can be associated with a user, a network device, a network environment, such as a home network environment, any other individual and/or system, or any combination thereof. The user data, the one or more profile configurations 250, the one or more user identifiers 260, or any combination thereof can be stored in any type of storage system including, but not limited to, a flat file system, a database, a table, a data structure, a data object, any other type of storage system, or any combination thereof.

The notification repository 308 can comprise any type of non-transitory computer-readable storage medium as discussed with reference to FIG. 2. The notification repository 308 can store multi-media data or any other data associated with, for example, one or more video notifications as discussed with reference to FIG. 5D. In one or more embodiments, the notification repository 308 is part of or included within the data aggregator 304 or any other component of the multi-modal portal application 350. The one or more video notifications can be stored in any type of storage system including, but not limited to, a flat file system, a database, a table, a data structure, a data object, any other type of storage system, or any combination thereof. In one or more embodiments, the notification repository is remote from the multi-modal portal application 350.

The analytics engine 302 can receive a request from the access portal 306. The request can be from one or more requestors, such as one or more network devices and/or one or more users associated with one or more network devices. The request can include a command to access user data, to store user data, or both, a user identifier or other identification associated with a user, and any other information. The analytics engine 302 can query the data aggregator 304 for the one or more profile configurations 250 associated with the one or more user identifiers 260. The analytics 302 can determine based on the one or more profile configurations 250 how to analyze the request. For example, the analytics engine 302 can compare the user identifier 260 to one or more profile configurations 250 and based on the comparison allow or deny the request. In one or more embodiments, the analytics engine 302 sends a prompt via the access portal 306 to the requestor (for example, a particular user and/or network device). The prompt can include a visual indication that the request has been processed (allowed) or denied. In one or more embodiments, the analytics engine 302 can include a notifications module that comprises one or more computer-readable instructions that when executed by a processor query the notification repository 308 and provide one or more video notifications to a multi-modal mesh hub 310 based on the profile configuration 250 associated with a client user.

The multi-modal mesh hubs 310 can comprise any one or more network devices that can form a mesh of data connectivity hubs, for example, as indicated by the dotted lines. In one or more embodiments, multi-modal mesh hub 310A comprises an access point device 2, multi-modal mesh hub 310B comprises an extender access point device 3, and multi-modal mesh hubs 310C, 310D, and/or 310E comprise a client device 4. In one or more embodiments, any one or more of the multi-modal mesh hubs 310C, D, and E can comprise one or more multi-sensor device 140. The multi-modal mesh hubs 310C, D, and E can be arranged to provide one or more redundant data paths for data, such as user data, received from one or more sensing device 5 and/or a client device 4. In one or more embodiments, any one or more of the multi-modal mesh hubs 310 can communicate with one or more other multi-modal mesh hubs via a Wi-Fi connection, for example, as indicated at multi-modal mesh hubs 310A, B and C. On one or more embodiments multi-modal mesh hubs 310D and E can communicate using any protocol, for example, any one or more short-range protocols, such as Bluetooth, Zigbee, LoRa, etc.

The multi-modal mesh hub 310A can interface or communicate with the access portal 306 so as to securely send a request to and/or receive a response from the multi-modal portal application 350 include, for example, data received from any one or more multi-modal mesh hubs 310. For example, the multi-modal mesh hub 310A may have an associated certificate that is transmitted along with any request to the multi-modal portal system 18 so that the multi-modal mesh hub 310A is properly authorized. The multi-modal mesh hubs 310 can work together as a virtual connectivity hub to communicate with the one or more client devices 4 and/or one or more sensing devices 5 of a network environment 300. For example, the one or more sensing devices 5 can comprise an optical instrument (such as a camera or other image capture device), a motion detector, any one or more diagnostic devices, one or more sensors, etc. The one or more sensing devices 5 can be securely paired with any one or more multi-modal mesh hubs 310 to establish a secure association.

In one or more embodiments, the multi-modal mesh hub 310A connects directly to the multi-modal portal system 18 via an external data connection, such as an Internet Wi-Fi connection. In one or more embodiments, the multi-modal mesh hub 310A, or any other multi-modal mesh hub 310, can connect to the multi-modal portal system 18 via LTE or cellular connection that does not rely on an Internet Wi-Fi connection. In one or more embodiments, the LTE or cellular connection is a backup connection for the Internet Wi-Fi connection. In one or more embodiments, the multi-modal mesh hub 310 can include a multi-sensor hub 150 and one or more multi-sensor devices 140 as discussed with reference to FIG. 14 such that multi-modal portal system 18 of the network environment 1400 operates or functions similar to that discussed with reference to FIG. 3.

Figure 4:
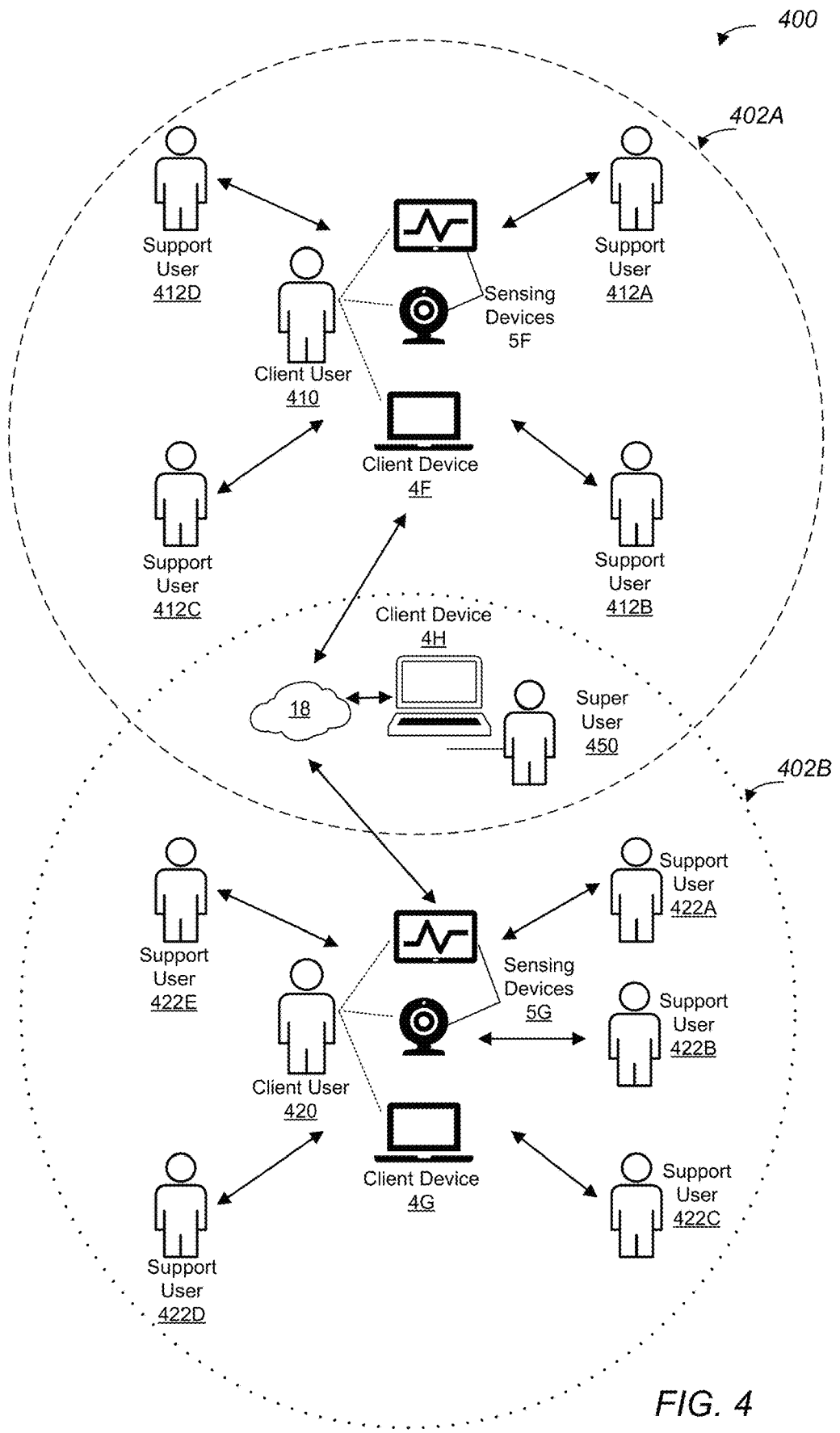
FIG. 4 is an illustration of a network environment for multiple multi-modal portal system networks, according to one or more aspects of the present disclosure.

FIG. 4 is an illustration of network environment 400 for multiple multi-modal portal system networks 402A and 402B, according to one or more aspects of the present disclosure. For example, an elderly user (such as a client user 410 or 420) can remain at home (aging-in-place) especially if given assistance from one or more support users (such as a support user 412 or 422) or trusted users (such as a super user 450, one or more support users 412 and/or 422, a family member, any other trusted user, or combination thereof). Assistance can have many forms including in-person or virtual assistance. Assistance can help an elderly user with maintaining regularity in aspects associated with the elderly user's environment, such as in taking prescribed medications or providing user data, for example, video or images of the elderly user. Providing more of a personalized reminder for such aspects can be beneficial in not only keeping an elderly user on track with a medical regimen but also with providing genuine engagement which reduces loneliness and can increase efficacy of the medical regimen. Such personalization can be in the form of pre-recorded video notifications stored in a notification repository 308 and availability to connect an elderly user, an isolated user, any other user that requires or needs monitoring, or any combination thereof with a trusted user based on a schedule or on-demand.

The network environment 400 can include one or more network devices for example, client devices 4F, 4G and 4H and/or sensing devices 5F and 5G, that are the same as or similar to the network environment 100 of FIG. 1, network device 200 of FIG. 2, and/or network environment 300 of FIG. 3. The network environment 400 can provide a closed secure support network where access is restricted based on one or more profile configurations 250 as discussed with reference to FIGS. 2 and 5A-5D. While the present disclosure discusses FIG. 4 in relation to one or more healthcare services, the present disclosure contemplates that any type of service can be associated with the network environment 400.

The network environment 400 can include one or more multi-modal portal system networks, such as multi-modal portal system networks 402A and 402B, collectively referred to as multi-modal portal system network(s) 402. Each multi-modal portal system network 402 can be associated with a client user, such as client user 410 and client user 420, a super user 450, and one or more support users 412A-412D (collectively referred to as support users 412), support users 422A-422E (collectively referred to as support users 422), one or more client devices 4F, 4G, and 4H (collectively referred to as client devices 4) one or more sensing devices 5A and 5B (collectively referred to as sensing devices 5), or any combination thereof. As an example, the network environment 400 can be associated with a healthcare services network environment for providing one or more healthcare services to one or more client users, such as client user 410 and client user 420.

A client user 410 of a multi-modal portal system network 402A can be associated with one or more sensing devices 5F (for example, one or more sensing devices 5 of FIG. 1) and one or more client devices 4F (for example, one or more client devices 4 of FIG. 1). One or more support users 412A, 412B, 412C, and 412D can be associated with the client user 410 for providing one or more healthcare services to client user 410. The one or more support users 412 can access, such as any of view, modify, alter, store, and/or manage, user data associated with client user 410 via the client device 4F based on a corresponding profile configuration 250. Client device 4F can be connected to a multi-modal portal system 18 such that client device 4F can send and receive user data associated with client user 410 to and from the multi-modal portal system 18.

A client user 420 of a multi-modal portal system network 402B can be associated with one or more sensing devices 5G (for example, one or more sensing devices 5 of FIG. 1) and one or more client devices 4G (for example, one or more client devices 4 of FIG. 1). One or more support users 422A, 422B, 422C, 422D, and 422E can be associated with the client user 420 for providing one or more healthcare services to client user 420. The one or more support users 422 can access, such as view, modify, alter, store and/or manage user data associated with client user 420 via the client device 4G based on a corresponding profile configuration 250. Client device 4G can be connected to a multi-modal portal system 18 such that client device 4G can send and receive user data associated with client user 420 to and from the multi-modal portal system 18. In one or more embodiments, a support user 412C can be remote from the client user 410 and can request a visual interface with the client user 410. The visual interface can be authorized by the multi-modal portal system 18 such that a visual interface connection, for example, a video call, is established between a network device associated with the support user 412C and client user 410.

Each of the client users 410 and 420 can be associated with a super user 450. Super user 450 can access user data associated with the client users 410 and 420 based on a corresponding profile configuration 250. The super user 450 can access the user data via a connection to the multi-modal portal system 18, for example, as discussed in reference to any one or more figures discussed herein, such as FIGS. 1-3, and 14. All of the user data associated with the client users 410 and 420 is exchanged within the closed multi-modal portal system networks 402A and 402B, respectively. In one or more embodiments, the one or more support users 410 and/or 420, the super user 450, any other user (for example, a designated user, a family member or near-and-dear), or a combination thereof can be a trusted user based, for example, on the profile configuration 250 associated with the client users 410 and/or 420.

In one or more embodiments, the network environment 400 is a healthcare services network. For example, multi-modal portal system network 402A can be a first healthcare network associated with a first patient (client user 410) and the multi-modal portal system network 402B can be a second healthcare network associated with a second patient (client user 420). The multi-modal portal system 18 can manage information associated with a user, for example, the client user 410 and the client user 420 based on one or more profile configurations 250. The one or more profile configurations 250 can comprise any of one or more user identifiers 260 associated with one or more client users and/or one or more network devices, one or more parameters, any other parameters, or any combination thereof. The one or more user identifiers 260 can comprise a unique identifier associated with a user, for example, client users 410 and 420 and/or a network device, for example, client devices 4.

The one or more profile configurations 250 can comprise one or more parameters. For example, FIGS. 5A-5D illustrate one or more profile configurations 250 for a multi-modal portal system 18, according to one or more aspects of the present disclosure. The one or more profile configurations 250 are associated with a healthcare services network, such as multi-modal portal system networks 402A and 402B. As illustrated in FIG. 5A, the one or more parameters of a profile configuration 250 can comprise one or more user profiles 502, one or more profile descriptions 504, one or more access parameters 506, one or more device identifiers 508, one or more encrypted credentials 510, one or more pre-authorization accesses 512, any other parameters associated with a user and/or network device, or a combination thereof.

The one or more user profiles 502 are associated with one or more users and/or network devices and can include, but are not limited to, any of a primary contact, a caregiver, a healthcare professional, a coordinator, a personal service, any other type of user and/or network device, or any combination thereof. In one or more embodiments, any of the one or more user profiles 502 can be designated as a trusted user. The one or more user profiles 502 can be associated with one or more profile descriptions 504 including, but not limited to, any of a family member, friend, and/or guardian, a personal staff member or nurse, a doctor, a care administrator, a general staff member, a trusted user, any other description, or a combination thereof as illustrated in FIG. 5B. The one or more user profiles 502 can be associated with one or more access parameters 506.

The one or more access parameters 506 can include the types of data that a user or a network device associated with a corresponding user profile 502 is allowed to access, such as to view, modify, store, manage etc. In one or more embodiments, the access parameters 506 can include any alphanumeric characters, a binary value, or any other value. For example, as illustrated, a "Yes" indicates access to the data while a "No" indicates that the data is not accessible by the corresponding user profile 502. In one or more embodiments, a binary "1" or "0" could be used. The one or more access parameters 506 can include, but are not limited to, any of a video call, an image data (such as from a camera), a diagnostic data (such as heart rate, blood pressure, oxygen level, weight, activity level, temperature, etc.), a sensor data, an activity data, a protected data, a pre-authorization data, any other type of data, or a combination thereof as illustrated in FIG. 5B. As an example, the pre-authorization data can indicate whether or not a pre-authorization is required to access the data by the associated user profile 502, can include a pre-authorization access 512, such as a code that indicates a pre-authorization value, that the associated user can receive responses from a client user 410 and/or 420, such as a response to a video notification 509 of FIG. 5D.

The creating or setting up of a profile configuration 250 can begin with assignment of roles to individuals and/or network devices (such as support users 412 and 422 or client devices 4F-4H) associated with a patient (such as client users 410 and 420). For example, referring back to FIG. 4, super user 450 can be associated with a user profile 502 of a healthcare professional, such as a doctor, that provides one or more healthcare services to client users 410 and 420 and has access to all healthcare related information associated with client user 410 and client user 420. Support users 412A and 422A can be associated with a primary contact user profile, support users 412B and 422B can be associated with a caregiver user profile, support users 412C and 422C can be associated with a coordinator user profile, and support users 412D and 422D can be associated with a personal services user profile. Each of the support users 412 and 422 have access as indicated by the associated access parameters 506. In one or more embodiments, the default setting for any one or more access parameters 506 is no access, for example, a "No". Any one or more default settings could be used for any one or more of the access parameters 506. In one or more embodiments, the one or more user profiles 502 can be updated or modified dynamically.

A user identifier 260 can also be associated with a device identifier 508 such that an encrypted credential 510, a per-authorization access 512, or both can be associated with a user profile 502, a device identifier 508, or both. An encrypted credential 510 can be utilized by the multi-modal portal system 18 to provide authorization of a request from a user associated with a user profile 502. The pre-authorization access 512 can be associated with a user profile 502 such that a user associated with the user profile 502 is pre-authorized to access user data, for example, pre-authorized to connect with a client user via a visual interface connection.

As illustrated in FIG. 5C, for each user profile 502 associated with a user identifier 260, one or more encrypted credentials 510 and/or one or more pre-authorization accesses 512 can be associated with the user profile 502, a device identifier 508, or both. In one or more embodiments, a device identifier 508 can be associated with a device name, a mobile application, a portal, any other type of device or resource, or any combination thereof. In one or more embodiments, the pre-authorization access 512 can be indicative of an authorization code or time period, such as a date and/or time, that pre-authorization is permitted.

As illustrated in FIG. 5D, a user identifier 260 can be associated with one or more scheduling parameters. The one or more scheduling parameters can include, but are not limited to, a task 503, a task instruction 505, a schedule 507, a video notification 509, an additional video notification 511, any other scheduling parameter, or a combination thereof. The task 503 can be indicative of an aspect or action associated with a user. For example, in the context of an aging-in-place environment, the task 503 can indicate a medication associated with the user as part of the user's medical regimen. Each task 503 can be associated with a task instruction 505. The task instruction 505 and the schedule 507 can include details associated with the task 503. For example, the task instruction 505 can correspond to a dosage and the schedule 507 can correspond to a frequency or occurrence for taking, consumption of, or performing a particular regimen, such as taking medication indicated by a task 503.

The video notification 509 can be associated with a task 503, The video notification 509 can include any of audio, video, a pre-recorded multi-media data, any other audio and/or video data, or any combination thereof for example, featuring a trusted user. The video notification 509 can be a personalized reminder regarding the task 503. Such a personalized reminder or message can be more persuasive, personal, or engaging than a default message that does not include a visual interface for viewing a trusted user's message. In one or more embodiments, the video notification 509 can be the same for one or more tasks 503. In one or more embodiments, the video notification 509 can also include text, such as a transcription of the audio portion of the video notification 509 so that while the multi-media data is played back the transcription is also displayed.

In one or more embodiments, the additional video notification 511 is the same as or similar to the video notification 509 except that the additional video notification 511 can include additional information associated with a schedule 507, a video notification to a response received from a user to a video notification 509, or both. For example, the additional video notification 511 can notify the user of the next scheduled video notification 509, provide additional information associated with the schedule 507, provide any other personalized message, or a combination thereof.

In one or more embodiments, any scheduling parameter can be associated with any one or more other scheduling parameters. For example, a task 503 can be associated with one or more task instructions 505, one or more schedules 507, one or more video notifications 509, and one or more additional video notifications 511, such as when a particular medication must be taken multiple times during a day, at different dosage levels throughout a day, any other basis, or any combination thereof. As another example, a first video notification 509 can include a Recording A and a Recording B while a second video notification 509 can include a Recording D and a Recoding B. Similarly, a first additional video notification 511 can comprise a Recording F while a second additional video notification 511 can comprise the same Recording F. In one or more embodiments, the video notification 509, the video notification 511 or both can include a personalized message from one or more trusted users or any other individual, entity or personnel.

While FIGS. 5A-5D illustrate one or more profile configurations 250 associated with a healthcare services network, the present disclosure contemplates that the one or more profile configurations 250 can be associated with any type of network. Additionally, the present disclosure contemplates that any one or more user profiles 502, one or more profile descriptions 504, one or more access parameters 506, one or more scheduling parameters, or any combination thereof can be added or deleted based on a particular network environment, including dynamically.

Figure 6:
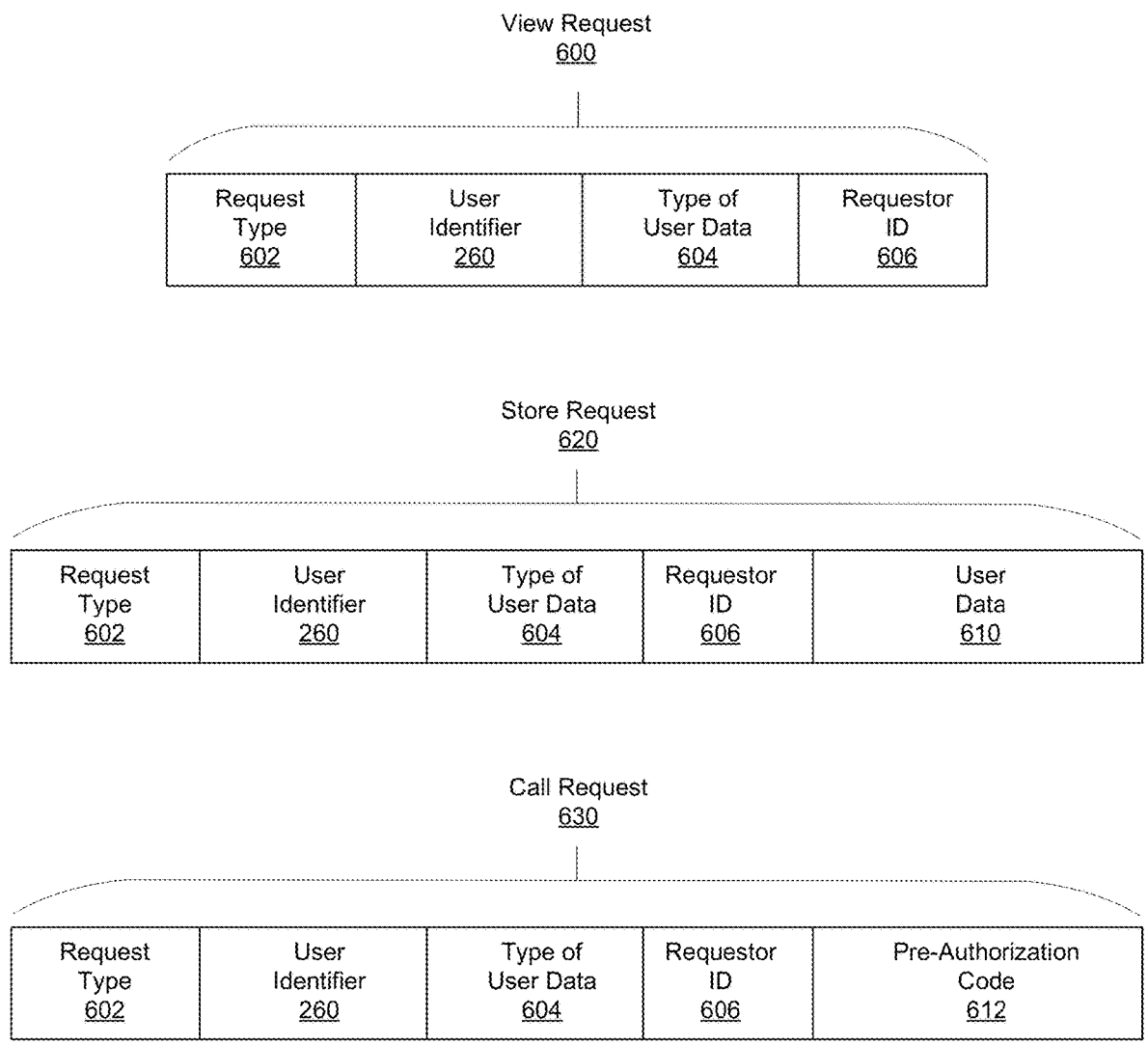
FIG. 6 illustrates exemplary requests associated with a multi-modal portal system, according to one or more aspects of the present disclosure.

All the data associated with client users 410 and 420 is securely communicated to the multi-modal portal system 18. For example, based on a profile configuration 250, each support user 412 or 422 can initiate via a client device 4F or 4G, respectively, a request to the multi-modal portal system 18. A request can comprise, for example, as illustrated in FIG. 6, a view request 600, a store request 620, or a call request 630 as well as any other type of request including, but not limited, to any of a modify request, a view request, a download request, a delete request, etc. A view request 600 can comprise any of a request type 602, a user identifier 260, a type of user data 604, a requestor identifier (ID) 606, any other information, or a combination thereof. A request type 602 can indicate that the request is a request to access user data associated with a user, for example, a client user 410 or 420, such as any of store, modify, view, delete, download, etc. The user identifier 260 can be indicative of a unique identifier, for example, that corresponds to the client user 410 or a client user 420, a support user 412 or a support user 422, a network device, or any combination thereof associated with the request. The type of user data 604 can be indicative of one or more access parameters 506 or any other type of data that a user associated with a user profile 502 can access such as view, modify, alter, store, manage, delete, etc.

The requestor ID 606 can be a unique identifier of a network, a multi-modal mesh hub 310, a client device 4 and/or a user associated with the view request 600. The requestor ID 606 may be required to ensure that the request is coming from a verified network or network device so as to ensure security and privacy of the user data. For example, a requestor ID 606 may prevent comingling of user data associated with a sensing device 5 that has been moved from one location to another or used with a new user without first being registered or otherwise associated with the different user and/or location. For example, with a healthcare services network, it is imperative that user data from a sensing device 5 only be associated with the intended patient or user. Requiring registration or association of the sensing device 5 prevents user data from incorrectly being stored or associated with the wrong user.

In one or more embodiments, the request type 602 is a request to store user data 610. In one or more embodiments, the store request 620 can include a request type 602, a user identifier 260, a type of user data 604, a requestor ID 606, and a user data 610. The user data 610 can comprise the data received from a sensing device 5, for example, data associated with the one or more access parameters 506. In one or more embodiments, the user data 610 can be encrypted for communication to the multi-modal portal system 18. In one or more embodiments an audit trail is generated, for any of the one or more requests 600, 620, 630, or any combination thereof, such that all access to, modification and/or storage of, etc. the user data 610 is recorded, for example, stored in a memory 24. In one or more embodiments, the audit trail comprises data or information associated with a visual interface or visual interface connection. The audit trail can be unalterable such that the audit trail provides an accurate representation of all requests associated with a user and/or user data.

In one or more embodiments, the call request 630 can include a request type 602, a user identifier 260, a type of user data 604, a requestor ID 606, and a pre-authorization code 612 Request type 602 can indicate that a visual interface connection is requested associated with user identifier 260. The type of user data 604 can indicate that a video or image is requested, such as that associated with an optical instrument (for example, a camera or smart camera). The requestor ID 606 can be associated with the support user or other user that is requesting a visual interference connection. In one or more embodiments, the pre-authorization code 612 can comprise a pre-authorization access 512, any other credential, or a combination thereof. In one or more embodiments, the pre-authorization code 612 can be used to inform an authorized consent provider of the pre-authorization of the associated user or to automatically provide for establishing the visual interface connection. In one or more embodiments, the pre-authorization code 612 is compared to a pre-authorization access 512 based on a pre-authorization access parameter of the one or more access parameters 506.

In one or more embodiments, the multi-modal portal system 18 can monitor the user data 610 received to determine if a threshold associated with, for example, an access parameter 506 or a type of user data has been reached (the user data 610 is at, exceeded or fallen below the threshold). In one or more embodiments, the analytics engine 302 of the multi-modal portal system 18 plots, graphs, averages, filters, applies any one or more mathematical functions or operations, or any combination thereof to the user data 610 as part of the threshold determination. In one or more embodiments, the multi-modal portal system 18 can send a notification to one or more users associated with a user profile 502 (for example, one or more client users 410 and/or 420, one or more support users 412 and/or 422, or a super user 450) based on the threshold determination. For example, the multi-modal portal system 18 can determine based on user data received from a motion sensor that the client user has fallen and can send a notification to an emergency response unit requesting assistance. In another example, a threshold can be associated with a time interval for user data associated with an access parameter. The multi-modal portal system 18 can determine that user data has not been received within the time interval threshold and send a notification to one or more users associated with a user profile.

Figure 7:
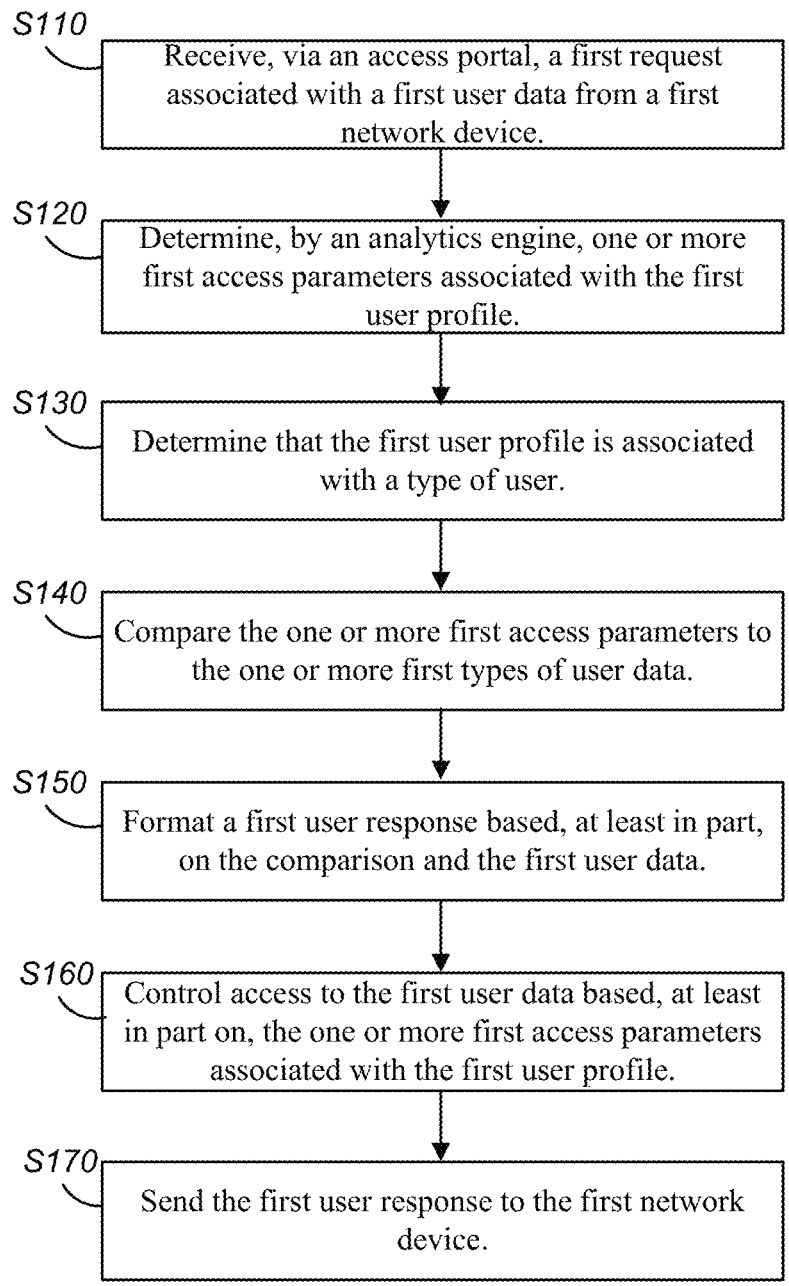
FIG. 7 is a flow chart illustrating a method for controlling access to user data, according to one or more aspects of the present disclosure.

FIG. 7 is a flow chart illustrating a method for configuration of one or more network devices, according to one or more aspects of the present disclosure.

The multi-modal portal system 18 may be programmed with one or more instructions such as a multi-modal portal application that when executed by a processor or controller causes the multi-modal portal system 18 to manage or control user data associated with one or more network devices and/or users in one or more embodiments. In FIG. 7, it is assumed that any one or more of the network devices include their respective controllers and their respective software stored in their respective memories, as discussed above in connection with FIGS. 1-4, which when executed by their respective controllers perform the functions and operations in accordance with the example embodiments of the present disclosure (e.g., including providing control of access to user data from one or more sensing devices 5).

The multi-modal portal system 18 comprises a controller 26 that executes one or more computer-readable instructions, stored on a memory 24, that when executed perform one or more of the operations of steps S110-S170. The multi-modal portal system 18 can comprise one or more software 25, for example, a multi-modal portal application. While the steps S110-S170 are presented in a certain order, the present disclosure contemplates that any one or more steps can be performed simultaneously, substantially simultaneously, repeatedly, in any order or not at all (omitted).

At step S110, the multi-modal portal system 18 receives, via an access portal 306, a first request associated with a first user data from a first network device, for example, a first sensing device 5. In one or more embodiments, a sensing device 5 is included within or coupled to a first client device 4. The client device 4 is connected to a network via an access point device 2 such that the client device 4 can communicate the first user data to the multi-modal portal system 18 via a connection between the access point device 2 and the ISP 1 and the ISP 1 and the multi-modal portal system 18. The first user data can be associated with a first client user, such as client user 410 or client user 420 of FIG. 4. To perform an authorization or verification for the first request, the first request can comprise a first user identifier 260 such that the first request is associated with a first user profile 502, for example, a first user profile 502 of a profile configuration 250. The first user data can comprise one or more first types of user data, for example, one or more types of user data associated with one or more sensing devices 5.

As discussed with reference to FIG. 6, the first request can comprise a view request 600 or a store request 620. In one or more embodiments, the first request can comprise any type of request including but not limited to, a view request, a store data request, a modify request, a download request, a delete request, any other type of request associated with a first user data, or any combination thereof.

At step S120, an analytics engine 302 of the multi-modal portal system 18 determines one or more first access parameters associated with the first user profile. For example, each user (such as support user 412 or support user 422 and/or a super user 450) can be associated with a unique user identifier 260 that is associated with a profile configuration 250. The profile configuration 250 provides the one or more access parameters 506 associated with a user profile 502 that is associated with the unique user identifier 260. The one or more first access parameters 506 limit the types of data that a user and/or a network device can access including, but not limited, any of viewing, modifying, altering, storing, managing, deleting, etc. any user data.

At step S130, the multi-modal portal system 18 determines that the first user profile is associated with a type of user. For example, the request can include a unique identifier 260 associated with a user. The unique identifier 260 can be associated with a profile configuration 250 that includes a user profile 502. The user profile 502 can indicate the type of user. For example, a support user 412 or a support user 422 can be associated with caregiver profile, a primary contact, a coordinator, etc. That is, each user and/or network device within a multi-modal portal system network can be associated with a user profile 502 such that the multi-modal portal system 18 can control access to user data based on the user profile 502.

At step S140, the multi-modal portal system 18 compares the one or more first access parameters 506 to the one or more first types of user data of the first request. For example, the first request can comprise a first type of user data associated with a first sensing device, such as a blood pressure monitor. The one or more types of data can correspond to one or more access parameters 506 associated with one or more user profiles 502 of a profile configuration 250. The user profile associated with the first request can indicate that diagnostic data is accessible or not accessible, such as viewable or not viewable, modifiable or not modifiable, storable or not storable, manageable or not manageable, etc. For example, as illustrated in FIG. 5B if a support user making the request is associated with a caregiver user profile, then the multi-modal portal system 18 can determine that diagnostic data is associated with the caregiver user profile.

At step S150, the multi-modal portal system 18 formats a first response to the first request based on the comparison of step S140 and the first user data. For example, if the first request is a view request 600, a first response can comprise the requested user data based on the type of user data 604 of the first request. As another example, if the first request is a store request 600, the first response can comprise a confirmation that the user data 610 of the store request 620 has been stored, for example, in a data aggregator 304.

At step S160, the multi-modal portal system 18 controls access to the first user data based on the one or more first access parameters 506 associated with the first user profile. For example, the analytics engine 302 can deny or allow access to the first user data. For example, if the comparison of step S140 indicates that the first user does not have a first user profile that permits access to the type of user data in the first request, the analytics engine 302 can deny the first request. Such denial can be indicated in the first response of step S150. Likewise, the analytics engine 302 can allow access if the comparison of step S140 so indicates and the first response of step S150 would then include the first user data sought by the first request.

At step S170, the multi-modal portal system 18 sends the first response to the first network device (for example, a client device 4) associated with the first request. For example, an access portal 306 of the multi-modal portal system 18 can interface with the client device 4, such as via an access point device 2 coupled to a client device 4, to communicate the first response. In one or more embodiments, the client device 4 comprises a user interface, such as a display, that displays the first response, such as a prompt received from the access portal 306.

In one or more embodiments, as discussed with reference to FIG. 4, multiple devices and multiple types of users can be associated with a user data. For example, a plurality of support users 412 or 422 and/or super user 450 can request access to user data associated with one or more users or subscribers, such as client users 410 and 420. The access portal 306 can thus receive a second request associated with a second user data from a second network device. For example, the first request can be associated with a support user 412A who is associated with a client user 410 while the second request can be associated with a support user 422 who is associated with a client user 420. The support user 412A can send the first request via a client device 4F while the support user 422A can send the second request via a client device 4G. The support user 412A is associated with a first user profile while the support user 422A is associated with a second user profile. In one or more embodiments, the first user profile and the second user profile can be the same, for example, both can be associated with a caregiver user profile. The analytics engine 302 can determine one or more second access parameters associated with the second user profile similar to or the same as step S120. Similar or the same as step S160, the access to the second user data is controlled based on the one or more second access parameters associated with the second user profile.

In one or more embodiments, the access portal 306 can receive a third request associated with the first user data and the second use data from a third network device. This third request can comprise a third user profile. For example, in reference to FIG. 4, the third network device can be client device 4H associated with a super user 450. The super user 450 can be associated with a third user profile, for example, a healthcare professional user profile 502. The super user 450 is included within multi-modal portal system networks 402A and 402B associated with client user 410 and client user 420, respectively. The analytics engine 302 can determine that the third user profile is associated with one or more third access parameters 506. For example, the healthcare professional user profile 502 of the super user 450 is associated with all of the access parameters 506 of FIG. 5B. That is, the super user 450 has a user identifier 260 that is associated with a first profile configuration 250 for a first user and a second profile configuration for a second user such that the super user 450 can access user data associated with both the first user and the second user. Thus, the analytics engine 302 can cause the access portal 306, for example, to send the first user data and the second user data to the third network device (client device 4H) based on the one or more third access parameters.

In one or more embodiments, with reference to FIG. 3, the multi-modal portal system 18 can receive from a multi-modal mesh hub (such as multi-modal mesh hub 310A) a store request 620 to store a third user data in the data aggregator 304. For example, client device 4F of FIG. 4 can be part of the multi-modal mesh hub 310. The third user data can be associated with a first client user, for example, client user 410A of FIG. 4. The store request 620 includes a user identifier 260 that identifies a support user 412A associated with a client user 410A and a requestor ID 606 that identifies the client device 4F. The analytics engine 302 can verify not only the support user 412 but also the client device 4F are authorized or permitted to access the user data based on the profile configuration 250. For example, the analytics engine 302 can compare the requestor ID 606 to one or more identifiers associated with the user identifier 260. For example, one or more profile configurations 250 can include an identifier associated with one or more network devices, one or more users, or both. The requestor ID 606 can then be compared to the one or more identifiers associated with one or more profile configurations 250 for the user identifier 260. If the verification is successful, the analytics engine 302 stores the third user data, for example, in any of the data aggregator 304, a cloud repository, any other storage medium, or a combination thereof. In this way, the multi-modal portal application can base verification of a request on both the network or the network device and the user making the request.

Figure 8:
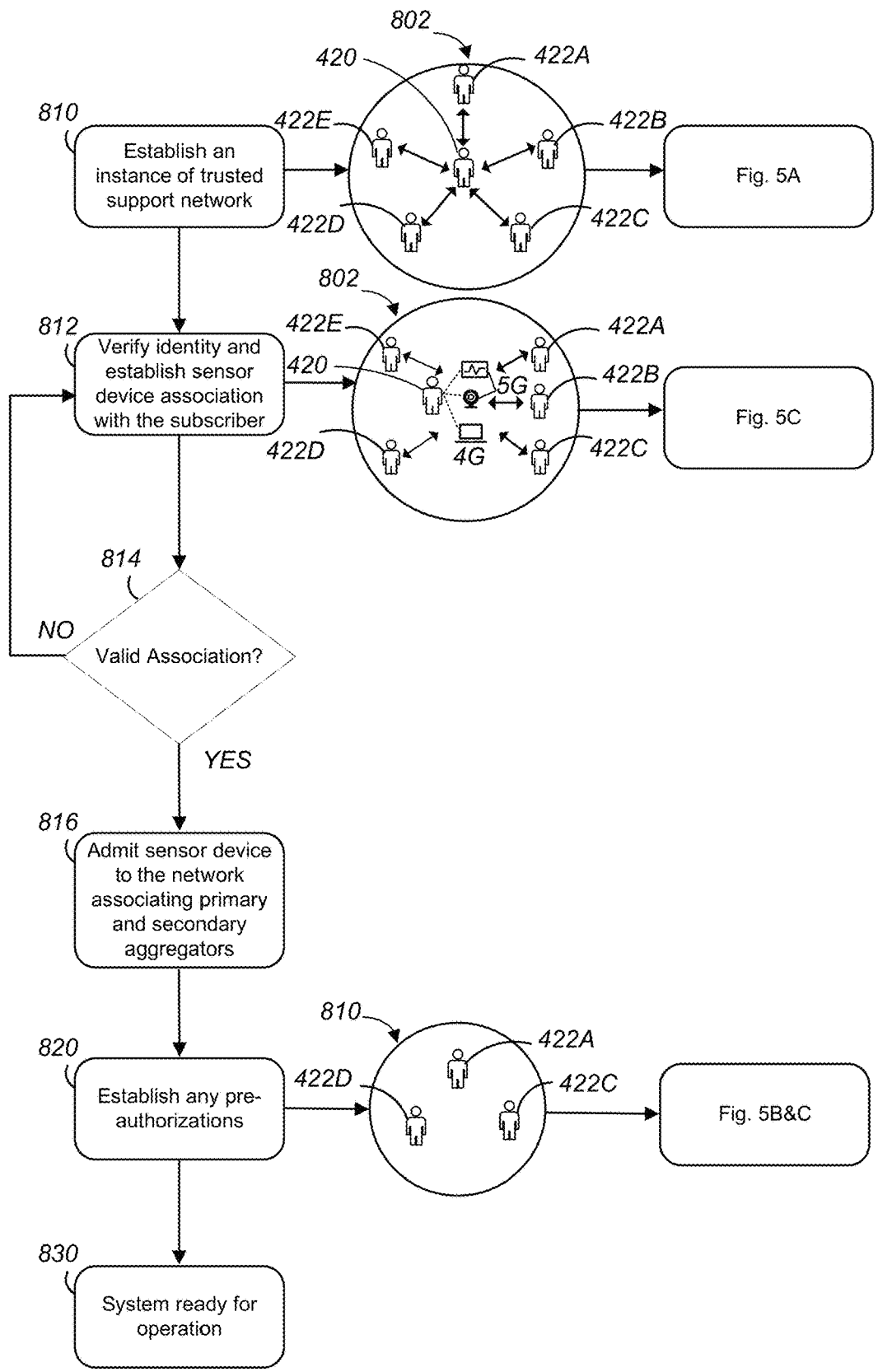
FIG. 8 illustrates preparation of a multi-modal portal system for operation, according to one or more aspects of the present disclosure.

FIG. 8 illustrates preparation of a multi-modal portal system 18 for operation, according to one or more aspects of the present disclosure. At aspect 810, the multi-modal portal application 350 establishes an instance of a trusted support network 802. The trusted support network 802 is centered around a client user 420 (for example, any of a patient, an elderly user, any other user that requires or needs monitoring, or a combination thereof). The client user 420 is associated with a user identifier 260 of a profile configuration 250. Within the trusted support network 810 are one or more support users 412A-412D (collectively referred to as support users 412) and/or 422A-422E (collectively referred to as support users 422) and one or more super users 450. In one or more embodiments, a support user 412 or 422, a super user 450, any other defined user associated with a user profile 502, or any combination thereof can be a trusted user, such as a primary contact 422A discussed with reference to FIG. 9. Each of the one or more support users 412/422 are associated with a user profile 502 that provides the access parameters 506 for each respective support user 412/422. In an example, a support user 422E can have an associated device identifier 508 that identifies one or more network devices, such as a client device 4, that the support user 422E utilizes to access user data associated with the client user 420. A support user 422 can also be associated with one or more encrypted credentials 510 that allow for verification of the access privileges of support user 422.

For example, a network comprises a mesh of data aggregators including a gateway, such as one or more multi-sensor devices 140 and a multi-sensor hub 150. The multi-sensor hub 150 can function as a gateway for a mesh network as well as a gateway to a cloud resource, such as a multi-modal portal system 18. The one or more multi-sensor devices 140 can serve as data aggregators for data received from one or more sensing devices 5. In one or more embodiments, a network comprises a single multi-sensor hub 150 and a plurality of multi-sensor devices 140 connected to the multi-sensor hub 150 via, for example, Bluetooth connection. The one or more multi-sensor devices 140, the multi-sensor hub 150, or any combination thereof can be associated with a client user 420 based on a profile configuration 250 associated with the client user 420.

At aspect 812, the identity of the one or more sensing devices 5G, the one or more multi-sensor devices 140, client devices 4G or any combination thereof are verified. For example, any one or more devices can be verified based on a device identifier 508, one or more encrypted credentials 510, a pre-authorization access 512, any other parameter associated with a user identifier 260 and/or a profile configuration 250 as illustrated in FIG. 5C. The any one or more devices can be associated with a support user 422, a client user 420, a super user 450, any other user associated with the client user 420, or any combination thereof. In one or more embodiments, the any one or more devices are verified based on an associated user profile 502, a user identifier 260, a device identifier 508, or any combination thereof as illustrated in FIG. 5A. As an example, a client user 420 is associated with a profile configuration 250 and a blood pressure meter sensing device 5 is associated with a device identifier 508 that is associated with the client user 420. The blood pressure meter sensing device 5 can be BLE capable with the device identifier 508 corresponding to the universally unique identifier (UUID) that identifies the type of device and manufacturer as well as one specific instance of the device as opposed to another instance. In one or more embodiments, the verifying indicates that a given device belongs to a specific environment, a specific user, or both, for example, that a biometric sensing device 5G is associated with a client user 420 at an environment 802.

At aspect 814, it is determined if the association of a device, such as the blood pressure meter sensing device 5, is valid, for example, such that the device can be associated with a mesh network, for example, the multi-modal mesh network of FIG. 3 and/or the network environment 1400 of FIG. 14. If the device is not validated, then process returns to aspect 812.

At aspect 816, the device, such as the blood pressure meter sensing device 5, is admitted to the network with a primary data aggregator and a second data aggregator being associated to the device. For example, after the relationship between the blood pressure meter sensing device 5 is derived at aspect 814, device is admitted to the network such that data can be collected by a data aggregator (such as the multi-sensor device 140). Based on a location of the device, for example, the blood pressure meter sensing device 5, a primary multi-sensor device 140 for a primary connection and a secondary multi-sensor device 140 for a secondary connection are associated with the device. As an example, the blood pressure meter sensing device 5 can be connected to the primary multi-sensor device 140 via a primary connection. The primary connection can be established by, in the context of BLE, pairing the blood pressure meter sensing device 5 with the first multi-sensor device 140. The primary multi-sensor device 140 can be selected as the primary data aggregator and the secondary multi-sensor device 140 as the secondary data aggregator based on one or more connectivity factors, such as distance, signal strength, load, number of connections, any other parameter, or any combination thereof). Additionally, the one or more connectivity factors can be compared to one or more corresponding thresholds as part of the selection. The secondary multi-sensor device 140 can be a back-up data aggregator. For example, the secondary multi-sensor device 140 can be an abstraction that the multi-sensor hub 150 maintains and manages such that data can be received even if a failure occurs at or with the primary multi-sensor device 140.

At aspect 820, the multi-modal portal application 350 establishes a pre-authorization for any one or more trusted users, one or more support users 412/422, one or more network devices (such as client devices 4) associated with the one or more support users 422, or both. Any one or more access parameters 506 can require a pre-authorization as indicated in FIG. 5B. The pre-authorization access 512 can be associated with a support user 422 to provide the necessary permissions for access to the one or more access parameters 506, such as a video call. For example, one or more support users 422A, 422C and 422D can be associated with a pre-authorization access 512 which provides on-demand privileges to a video call with the client user 420 such that the client user 420 is not required to affirmatively or expressly provide consent for the video call. In one or more embodiments, an authorized consent provider, such as a primary contact, can be notified that such a drop-in or on-demand video call is or has occurred without requiring that the primary contact provide any consent or authorization for the video call. Support users 422B, 422D and 422E are not provided with a pre-authorization access 512. An authorized consent provider or other identified user type is contacted or notified to obtain an authorization prior to allowing a drop-in video call with the client user 420. In one or more embodiments, the authorized consent provider is any of the one or more users associated with a user profile 502, an entity or service associated with a client user, any other designated user and/or entity, or any combination thereof. At aspect 830, the multi-modal portal application or multi-modal portal system 18 is ready for operation to control or provide access to user data within the trusted support network 802.

Figure 9:
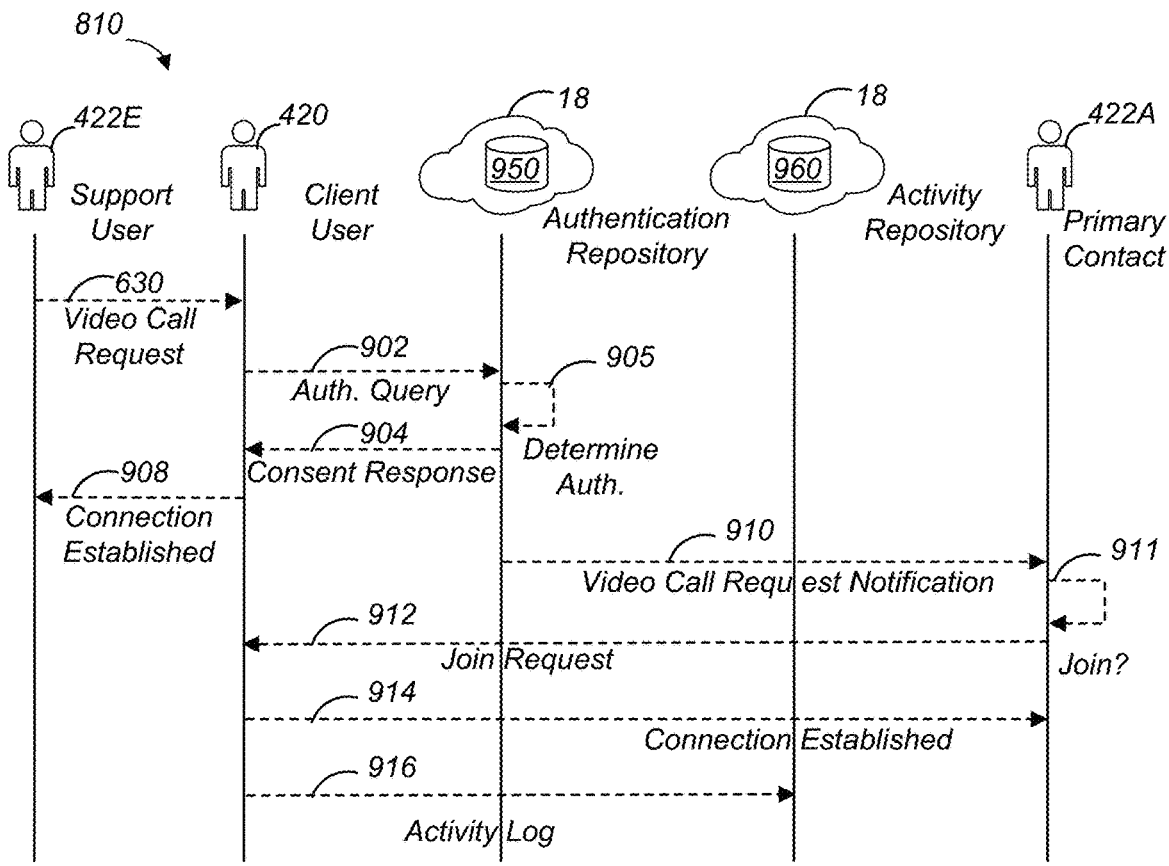
FIG. 9 illustrates a process for a visual interface request authorization, according to one or more aspects of the present disclosure.

FIG. 9 illustrates a process for a visual interface request authorization, according to one or more aspects of the present disclosure. A visual interface request can comprise a request to establish a visual interface connection, for example, via an optical instrument. In one or more embodiments, the visual interface request is a video call request 630 initiated by a support user 412E for a client user 410. In an example, the trusted support network 802 can be a caregiver-patient network that includes a patient/callee (client user 420), a caregiver/caller (support user 422E), and an authorization content provider (primary contact 422A). The patient/callee can be a in a challenged position such that providing express consent to access associated user data is not practical or cannot be achieved. The caregiver/caller can be, for example, any healthcare professional or service provider. To provide efficient and timely care, the caregiver/caller can remotely monitor the patient/callee.

The caregiver/caller can initiate a drop-in video call request 630 to a client device 4 associated with the patient/callee. The client device 4 can, for example, comprise a smart camera that is positioned within view of the patient/callee and securely associated with the patient/callee. The user identifier 260 associated with the patient/callee can include a device identifier 508 associated with the smart camera such that the identity of the smart camera can be confirmed and/or verified as a trusted device. The video call request 630 can come from a network device associated with the caregiver/caller, such as a laptop, mobile phone, or any other electronic device. This network device can be associated with a device identifier 508 such that the network device can be confirmed and/or verified as a trusted device. For example, once the network device is approved as a trusted device, authorization may not be required for additional calls based on the profile configuration 250.

Once the smart camera receives the video call request 630, the smart camera sends an authentication query 902 based on the video call request 630 to an authentication repository 950 of a multi-modal portal system 18. In one or more embodiments, the video call request 630 is sent directly to the authentication repository 950 and can include an authentication query 902. The authentication repository can have access to the associated profile configuration 250. The authentication repository 950 determines an authorization 905 for the authorization query 902 based on the associated profile configuration 250 and sends a consent response 904 to the smart camera. The consent response 904 can include the authorization 905, for example, any of an authorization code, a time-stamp, one or more credentials, a token, any other parameter, or any combination thereof. The smart camera establishes a connection 908 with the network device associated with the caregiver/caller. In one or more embodiments the connection 908 is established by the multi-modal portal system 18 based on the authorization 905. For example, the multi-modal portal system 18 sends a command or instruction to the smart camera, the network device associated with the caregiver/callee, or both to establish the connection 908.

In one or more embodiments, the authorization query 902 triggers a video call request notification 910, for example, when the network device, the caregiver/caller, the smart camera, or any combination thereof are not pre-authorized for a video call. The video call request notification 910 is sent to a consent provider device associated with an authorized consent provider, for example, a primary contact 422A. The authorized consent provider can, for example, be a family member, a super user 410, any other user that has privileges to provide authorization for one or more access parameters 506 associated with the user data. The consent provider device can be any type of network or electronic device, such as a laptop, a mobile phone, etc. The authorized consent provider can provide to the authentication repository 950 the authorization for the video call request 630. In one or more embodiments, the authorized consent provider can send a join request 912 to the smart camera to join the video call associated with the video call request 630. The smart camera can send a connection established 914 to the authorized consent provider to acknowledge the join request.

In one or more embodiments, any activity associated with a patient/callee can be required to be logged. An activity log 916 can be sent to an activity repository 960 associated with the multi-modal portal system 18. Each request, connection, authorization, any other activity, or any combination thereof can be stored in the activity repository 960 as an audit trail or log. In one or more embodiments, any of the authentication repository 950, the activity repository 960, or both can be local to or remote from the multi-modal portal system 18.

In one or more embodiments, the authorization provided at any stage of FIG. 9 can be a one-time authorization for the specific video call request 630, a persistent authorization such that the caregiver/caller need not request authorization for a period of time, the associated network device, or both.

Figure 10:
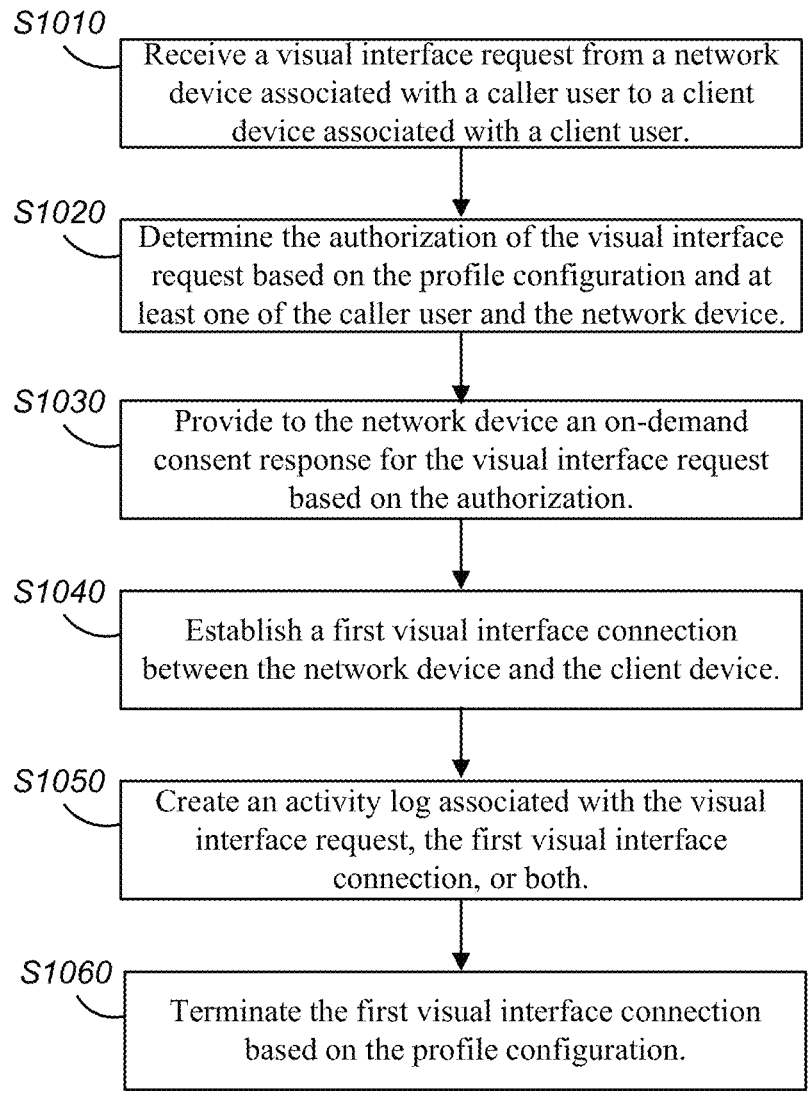
FIG. 10 is a flow chart illustrating a method for providing on-demand an authorization to a visual interface request, according to one or more aspects of the present disclosure.

FIG. 10 illustrates is a flow chart illustrating a method for providing on-demand authorization to a video interface request, according to one or more aspects of the present disclosure. While the steps S1010-S1060 are presented in a certain order, the present disclosure contemplates that any one or more steps can be performed simultaneously, substantially simultaneously, repeatedly, in any order or not at all (omitted).

At step S1010, a multi-modal portal system 18 (for example, that comprises a multi-modal portal application 350) receives, via an access portal 306, a visual interface request (such as a video call request 630) from a caller user (such as a support user 422 or 412) to a client device 4 associated with a client user (such as a client user 410 or 420). The client user can be associated with a profile configuration 250. The caller user and the client user can be part of a trusted support network 802 such that the profile configuration 250 associated with the client user provides privileges for access to one or more access parameters 506, including the required authorization for a visual interface request.

At step S1020, an analytics engine 302 of the multi-modal portal system 18 determines the authorization of the visual interface request based on the profile configuration 250 associated with the client user and at least one of the caller user and the network device. For example, the caller user, the network device, or both can be associated with a pre-authorization access 512 or can require that an authorized consent provider be contacted to provide the required authorization. In one or more embodiments, the multi-modal portal system contacts an authorized consent provider associated with the user profile to obtain the required authorization. The authorized consent provider sends the consent for the visual interface request to the multi-modal portal system 18.

At step S1030, the multi-modal portal system 18 provides the network device associated with the caller user with an on-demand consent response (such as consent response 904) for the visual interface request based on the authorization. The on-demand consent response can include one or more credentials required by the client device to establish a connection with the network device so as to enable a video call, for example, the consent received from the authorized consent provider. In one or more embodiments, the on-demand consent response is provided to the network device via the client device such that the multi-modal portal system 18 communicates with the network device via the client device. In one or more embodiments, the multi-modal portal system 18 communicates directly with the client device, the network device, or both.

At step S1040, the multi-modal portal system 18 establishes the first visual interface connection between the network device and the client device. The first visual interface connection can be established based on any of the profile configuration 250, the authorization, the on-demand consent response, any other parameter, or any combination thereof. The first interface connection can be established, for example, by providing one or more credentials to the network device, the client device or both. In one or more embodiments, the multi-modal portal system 18 establishes the first visual interface connection by sending an instruction or command to the client device to initiate or allow the visual interface associated with the visual interface request.

In one or more embodiments, the multi-modal portal system 18 can activate an optical instrument associated with the client device. For example, the client device can include a smart camera or can be connected to a smart camera. The multi-modal portal system 18 can send an instruction or a command to the client device that causes the smart camera to activate. The instruction or the command that causes the activation can include any of a turn-on command, an alter or modify position command (such as rotate, change angle, etc.), a focus command, any other command associated with an optical instrument, or any combination thereof. In one or more embodiments, the notification to the authorized consent provider can include a connection to the optical instrument such that the authorized consent provider can alter the or modify the optical instrument so as to provide the caller user with a visual of the client user. In one or more embodiments, the multi-modal portal system 18 allows the caller user to alter or modify the optical instrument.

In one or more embodiments, the authorized consent provider can request to join the visual interface between the client user and the caller user. The multi-modal portal system 18 can receive a join request from the authorized consent provider and can establish a second visual interface connection between a consent provider device associated with the authorized consent provider the client device associated with the client user. In this way a three-way communication is created between the client user, the caller user and the authorized consent provider. For example, if a caregiver seeks to establish a video call with a patient, a primary contact can be sent a notification that requests authorization for the video call. The primary contact can provide the authorization and, if desired, can join the video call. The primary contact can thus be part of any one or more video calls with the client user.

At step S1050, the multi-modal portal system 18 creates an activity log associated with the visual interface request, the first visual interface connection, any other user data associated with any other request, or any combination thereof. For example, an activity log can be created and stored in an activity repository 960. The activity log can be an audit trail of all activity associated with a user, for example, any activity associated with access to any one or more access parameters 506 associated with a given client user. In this way, all activity related to the client user can be tracked. The activity log can be created in real-time, periodically, or based on any other trigger or parameter.

At step S1060, the multi-modal portal system 18 can instruct the client device to terminate the first visual interface connection based on the user profile. In one or more embodiments, the multi-modal portal system 18 can establish the first visual interface connection for a specific time period. For example, a profile configuration 250 for a client user can establish that a caregiver can request a video call with the client user during a specified time period and at the end of the specified time period any video call in progress can be terminated. For example, a video call can automatically be requested and if authorized the video call connection can be authorized and then automatically terminated at the end of the specified time period.

In one or more embodiments, a profile configuration 250 is created for the client user prior to or during any one or more steps of FIG. 10, for example, as discussed with respect to FIG. 8. In one or more embodiments, the multi-modal portal system 18 creates a profile configuration associated with the client user. The caller user can be associated with a user profile 502 of the profile configuration 250 associated with the client user, the network device associated with the caller user, or both. One or more pre-authorizations associated with the user profile 502 can be based on at least one of the caller user, the network device or both. The authorization provided for the visual interface request at step S1030 can be determined based on the one or more pre-authorizations associated with the user profile. Such can allow for an authorization to automatically be provided without having to first notify the authorized consent provider. Additionally, the notification to the authorized consent provider can include the pre-authorization access 512 so that the authorized consent provider can base the consent response on the pre-authorization access 512.

Figure 11:
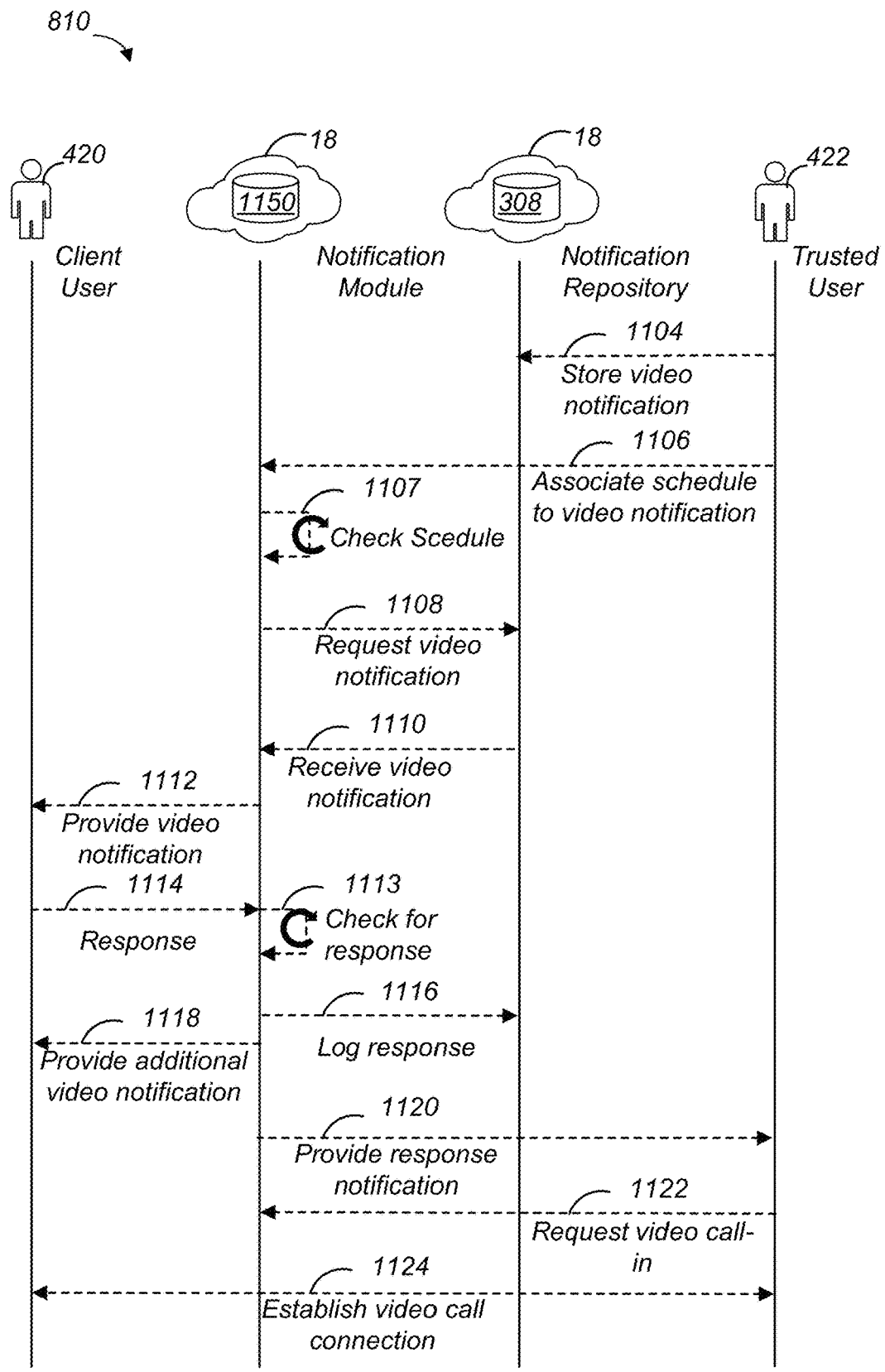
FIG. 11 illustrates a process for providing a video notification to a client device associated with a client user, according to one or more aspects of the present disclosure.

FIG. 11 illustrates a process for providing a video notification 509 to a multi-sensor hub 150, a client device 4, or both associated with a client user (such as a client user 410 or a client user 420 of FIG. 4), according to one or more aspects of the present disclosure. In one or more embodiments, the video notification 509 can be provided to client user 420 as a video call as discussed with reference to FIG. 9.

A trusted user can be a support user 412/422, a super user 450, a primary contact, any other user with an associated user profile 502 or any combination thereof. In the example of FIG. 11, the trusted user is a support user 422 and is referred to as trusted user 422. The trusted user 422 can create one or more video notifications 509. A network device 200, such as any of a laptop, a computer, any other device discussed with reference to client device 4, any other type of electronic device, or a combination thereof can be associated with the trusted user 422. A network device 200 can be associated with a device identifier 508 so as to have the proper credentials and authorization (such as encrypted credentials 510 and pre-authorization access 512) to access any user data including to create one or more scheduling parameters. For example, the trusted user 422 can send via the network device 200 a store video notification request 1104 to a notification repository 308 of a multi-modal portal system 18. The video notification request 1104 can include a video notification 509, an additional video notification 511, or both. The trusted user 422 can send via the network device 200 an associate a schedule to video notification request 1106 to the notification module 1150 of the multi-modal portal system 18 so as to associate the video notification 509, the additional video notification 511, or both with one or more other scheduling parameters as discussed with reference to FIG. 5D. For example, the associate schedule to video notification request 1106 can associate the video notification 509, the additional video notification 511, or both with one or more tasks 503, one or more corresponding task instructions 505, one or more schedules 507, or any combination thereof.

Once the scheduling parameters are set up or created as discussed with reference to FIG. 5D, the notification module 1150 can perform a determination or check 1107 of the one or more scheduling parameters. For example, the notification module 1150 can query the one or more schedules 507 based on a trigger, a timer, a semaphore, a periodic query, a timer interval, any other basis, or a combination thereof to determine a match to a criteria, such as a current data, a current time, a current day of week, any other criteria, or a combination thereof. For example, a schedule 507 can indicate a schedule of 9:00 AM each day of the week that is associated with a task 503, such as a Prescription #1, and a task instruction 505, a Dosage #1 as illustrated in and discussed with reference to FIG. 13. In one or more embodiments, one or more triggers can be set for each one or more schedules 507.

The notification module 1150 can identify based on the query or trigger one or more schedules 507 associated with a client user 410 and/or 420 as indicated by the associated profile configuration 250. For example, the notification module 1150 can identify a first schedule 507, such as Schedule #1. The notification module 1150 can send a request video notification query or request 1108 to the notification repository 308 for at least a video notification 509 associated with the first schedule 507. The notification module 1150 can receive a video notification instruction 1110 from the notification repository 308 that includes at least the video notification 509 associated with the first schedule 507. The notification module 1150 provides a video notification instruction 1112 to the client user 420 that includes the video notification 509. The video notification 509, for example, can include a personalized reminder from the trusted user 422 associated with the schedule 507. In one or more embodiments, the video notification 509 can include any type of data including multi-media data. The video notification instruction 1112 can also include data associated with the corresponding task 503, the corresponding task instruction 505, or both. For example, a text message, a video message, a verbal message, or any combination thereof can be presented to the client user 420 before, during, after, or any time throughout the presentation of the video notification 509 to the client user 420. As illustrated in FIG. 13, a multi-sensor hub 150 can be connected to a display device, such as a client device 4, that includes a user interface 20 or a display device for displaying a video notification instruction 1112 received by the multi-sensor hub 150. In one or more embodiments, the multi-sensor hub 150 includes a camera or a visual interface. In one or more embodiments, the multi-sensor hub 150 is connected to a sensing device that comprises a camera or a visual interface. The video notification instruction 1112 can include a personalized message, a video notification 509, any other message from a trusted user 422, the associated schedule 507, the associated task 503, and the associated instruction 505.

The notification module 1150 can continuously, periodically, or at timed intervals perform a check 1113 for a response from the client user 420 to the video notification instruction 1112. The client user 420 can respond with a response 1114 to the video notification instruction 1112. The response 1114 can comprise a video response, a verbal-only response, or a non-responsive response. In one or more embodiments, the response 1114 can indicate an acknowledgement of the video notification 509 or additional video notification 511, such as an affirmation, a decline of any message or notification, or any other response from the client user 420. For example, the client user 420 in response to a video notification 509 to take a Medication #1 can send a video response, a verbal response, a text-based response, or any other type of response that indicates a status, such as the Medication #1 has been taken as instructed, has not been taken, any other status, or a combination thereof.

The notification module 1150 can perform a log response 1116. For example, the log response 1116 can include creating or maintaining a log of all activity associated with the client user 420, for example, similar to or the same as the activity log 916 discussed with reference to FIG. 9. The activity logged can include a timestamp and corresponding identifier for all notifications sent to and responses received from the client user 420. In this way, a trusted user 422 or any other user with appropriate authorization can review all activities associated with the client user 420, for example, to confirm conformance to the prescribed medical regimen.

The notification module 1150 can in response to the response 1114 from the client user 420 or automatically provide an additional video notification instruction 1118. For example, if the response 1114 indicates that the client user 420 has not taken the Medication #1, the notification module 1150 can query the notification repository 308 for any associated additional video notification 511. The additional video notification instruction 1118 can include the associated additional video notification 511. The additional video notification 511 can include another personalized message from the trusted user 422 or any other user that, for example, encourages compliance with the medical regimen.

The notification module 1150 can provide a response notification 1120 to a trusted user 422. The response notification 1120 can include or indicate a response from the client user 420 to the video notification 509, the additional video notification 511, or both. In response to the response notification 1120, the trusted user 422 can send a video call-in request 1122 to the notification module 1150. The video call-in request 1122 can also be sent to the notification module 1150 at any time, for example, as discussed with reference to FIG. 9. In response to the video call-in request 1122 the notification module establishes a video call connection 1124 between the client user 420 and the trusted user 422, for example, as discussed with reference to FIG. 9.

Figure 12:
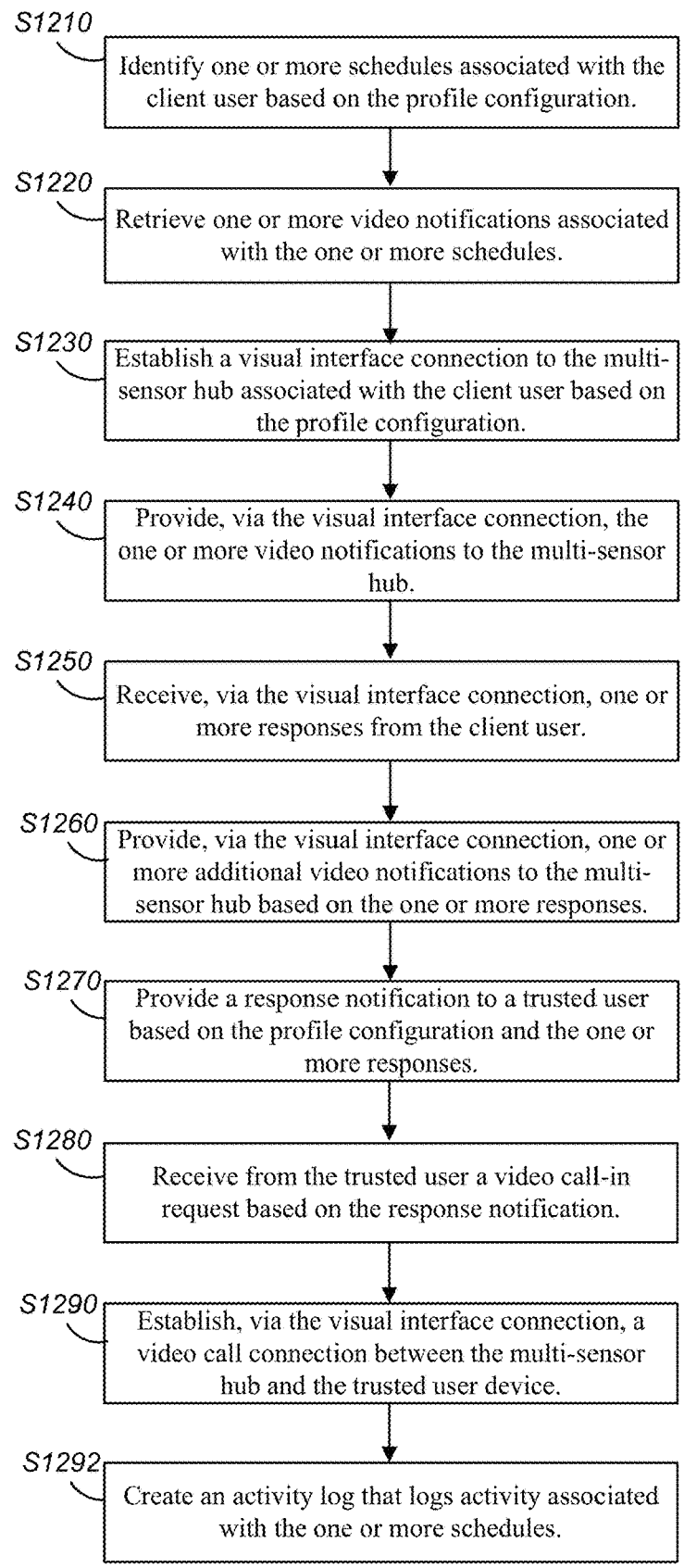
FIG. 12 is a flow chart illustrating a method for providing one or more video notifications to a multi-sensor hub based on a profile configuration associated with a client user, according to one or more aspects of the present disclosure.

FIG. 12 is a flow chart illustrating a method for providing one or more video notifications to a multi-sensor hub 150 based on a profile configuration associated with the client user 410/420, according to one or more aspects of the present disclosure. A multi-modal portal system 18 may be programmed with one or more instructions such as a multi-modal portal application that when executed by a processor controller causes the multi-modal portal system 18 to manage or control user data associated with one or more network devices and/or users in one or more embodiments. In FIG. 12, it is assumed that any one or more of the network devices include their respective controllers and their respective software stored in the respective memories, as discussed herein in connection with any one or more figures, such as FIGS. 1, 3-11, 13, 14, and 15, which when executed by their respective controllers perform the functions and operations in accordance with the example embodiments of the present disclosure (e.g., including providing a video notification to a client user).

The multi-modal portal system 18 comprises a controller 26 that executes one or more computer-readable instructions, stored on a memory 24, that when executed perform one or more of the operations of steps S1210-1292. The multi-modal portal system can comprise one or more software 25, for example, a multi-modal portal application 350. While the steps S1210-S1292 are presented in a certain order, the present disclosure contemplates that any one or more steps can be performed simultaneously, substantially simultaneously, repeatedly, in any order or not at all (omitted).

At step S1210, the multi-modal portal system 18, such as an analytics engine 302 and/or a notification module 1150 of a multi-modal portal application 350, identifies one or more schedules associated with the client user 410 and/or 420 based on a profile configuration 250 that is associated with the client user. The profile configuration 250 can be created or set up using any one or more user interfaces or other input mechanism that interfaces with or to the multi-modal portal application 350, for example, via an analytics engine 302. For example, the multi-modal portal system 18 can be instructed, for example, by a user via a user interface 20, to create a profile configuration 250 associated with the client user 410 and/or 420. In one or more embodiments, the client user 410 and/or 420 utilizes a user interface 20 of a client device 120 that is communicatively coupled to the multi-modal portal system 18 (such as, via one or more connections) to create the profile configuration 250. In one or more embodiments, any authorized user or user with access to the multi-modal portal system 18 can initiate or create a profile configuration 250 associated with a particular client user 410 and/or 420. For example, a family member and/or a primary caregiver (such as a doctor) can initiate or create a profile configuration 250 associated with a particular client user 410 and/or 420. The multi-modal portal system 18 can then associate a trusted user with the profile configuration 250. The multi-modal portal system 18 can also associate any type of electronic or network device with the client user, for example, client device 120, a multi-modal mesh hub 310, a multi-sensor hub 150, a multi-sensor device 140, a sensing device 5, or any other device connected to a network associated with the client user 410 and/or 420. The multi-modal portal system can associate one or more scheduled notification with the client user 410 and/or 420 and then associate one or more video notification with the one or more scheduled notifications.

At step S1220, the multi-modal portal system 18, for example via the analytics engine 302, an access portal 306 or both of the multi-modal portal application 350, retrieves one or more video notifications associated with the one or more schedules. In one or more embodiments, the one or more video notifications can be stored in a repository within or coupled to the multi-modal portal system 18, for example, a notification repository 308. The one or more video notifications can allow a client user 410 and/or 420 to be reminded of, for example, a medical regimen, receive personalized messages from a near-and-dear or family member, any other purpose, or any combination thereof. Such a video notification can prevent a client user 410 and/or 420 from feeling isolated or provide clarification in instructions to the client user 410 and/or 420.

At step S1230, the multi-modal portal system 18, for example, via the analytics engine 302, the access portal 306, or both, can establish a visual interface connection to a multi-sensor hub 150 associated with the client user 410 and/or 420 based on the profile configuration 250. For example, as illustrated in FIG. 14, the multi-modal portal system 18 can communicate with the multi-sensor hub 150 via an access point device 2.

At step S1240, the multi-modal portal system 18, for example, via the analytics engine 302, the access portal 306 or both, can provide via the visual interface connection the one or more video notifications to the multi-sensor hub 150. For example, the multi-sensor hub 150 can be coupled to or include a display device, one or more speakers, and/or any other device for playback of a video notification, such as a television or monitor as illustrated in and discussed with reference to FIG. 13. The one or more video notifications can include any type of information, including, but not limited to, multi-media information.

At step S1250, the multi-modal portal system 18, for example, via the analytics engine 302, the access portal 306, or both, can receive via the visual interface one or more responses from the client user 410 and/or 420, for example, via the multi-sensor hub 150. The one or more responses can take any form including a visual response (such as a motion by the client user 410 and/or 420), an audio response, and/or an audio/visual response. In one or more embodiments, the multi-sensor hub 150 includes a video receiver, such as a camera, or is connected to a video receiver within a proximity to the client user 410 and/or 420. For example, the multi-sensor hub 150 that includes a video receiver can be positioned such that identification of and receiving of the response from the client user 410 and/or 420 is possible At step S1260, the multi-modal portal system 18, for example, via the analytics engine 302, the access portal 306, or both can provide via the visual interface connection one or more additional video notifications to the multi-sensor hub 150 based on the one or more response. The client user 410 and/or 420 can signal a response or communicate a response via the visual interface connection that is associated with one or more additional video notifications. For example, the client user 410 and/or 420 can indicate that any of the video notification was not understood, additional information is required, the video notification was received, the instructions associated with the video notification were completed, a null response (such as expiration of a timer prior to the client user 410 and/or 420 providing a visual, audio, or both response), any other response, or any combination thereof. In response, the multi-modal portal system 18 can provide the one or more additional video notifications. In one or more embodiments, one or more additional video notifications can be provided any number of times with or without receiving a response associated with the client user 410 and/or 420.

At step S1270, the multi-modal portal system 18, for example, via the analytics engine 302, the access portal 306, or both provides a response notification to a trusted user based on the profile configuration 250 and the one or more responses. For example, the profile configuration 250 associated with the client user 410 and/or 420 identifies a trusted user associated with the client user 410 and/or 420. One or more settings of the profile configuration 250 can indicate when the trusted user should be notified or contacted, such as when the one or more responses indicate an issue or that additional assistance is requested or needed by the client user 410 and/or 420.

At step S1280, the multi-modal portal system 18, for example, via the analytics engine 302, the access portal 306, or both, receives from the trusted user a video call-in request based on the response notification. The profile configuration 250 associated with the client user 410 and/or 420 can indicate that such a video call-in request is authorized for the trusted user. For example, the multi-sensor hub 150, the multi-modal mesh hub 310, or any other network device coupled to either can be functional or operational to initiate and connect a video call-in.

At step S1290, the multi-modal portal system 18, for example, via the analytics engine 302, the access portal 306, or both can establish via the visual interface connection, a video call connection between the multi-sensor hub 150 and a network device associated with the trusted user (such as a trusted user device identified as authorized in the associated profile configuration 250, for example, by device identifier 508 as discussed with reference to FIG. 5C).

At step S1292, the multi-modal portal system 18, for example, via the analytics engine 302, can create an activity log that logs activity associated with the one or more schedules, such as any one or more of the steps S1210-S1290. For example, the multi-modal portal system 18 can store the activity log in a repository of or associated with the multi-modal portal application 350, such as data aggregator 304. The activity log can include, but is not limited to, any of a recording of the video-call, a timestamp, a date stamp, a recording of the one or more responses, an identifier associated with the one or more video notifications and/or additional video notifications, any other activity, or a combination thereof.

Figure 16A:
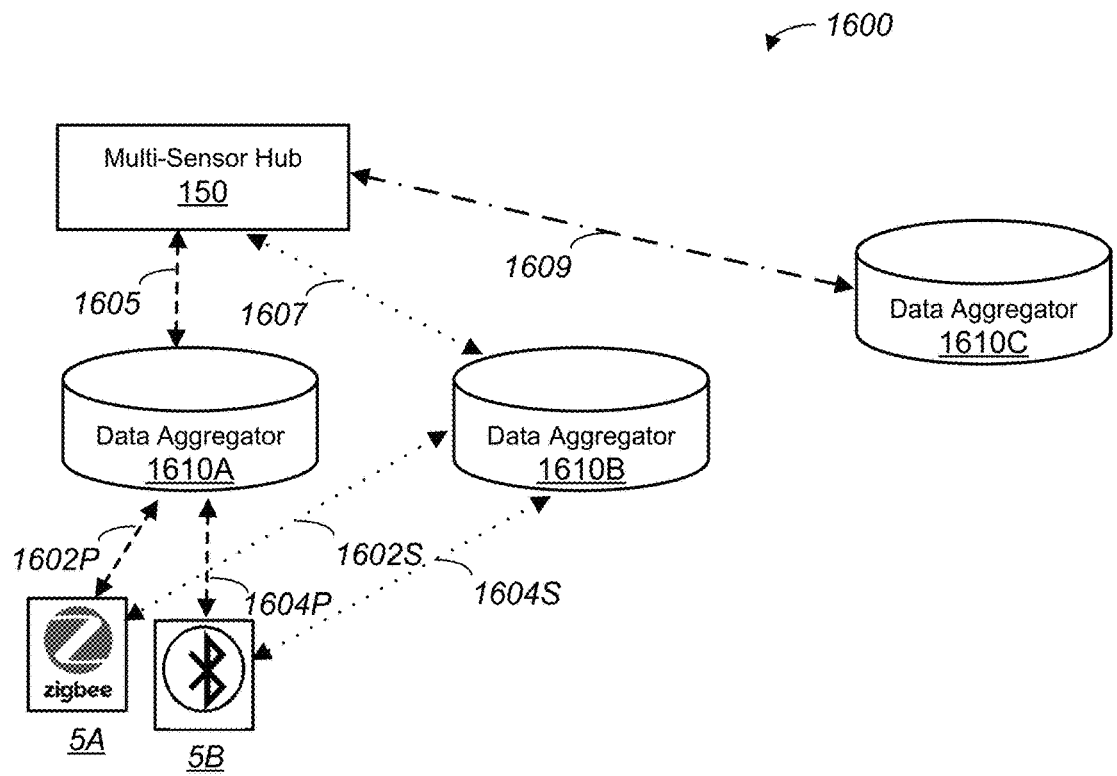
FIGS. 16A and 16B illustrate a process for altering a data path of one or more devices in a network 1600, according to one or more aspects of the present disclosure.
Figure 16B:
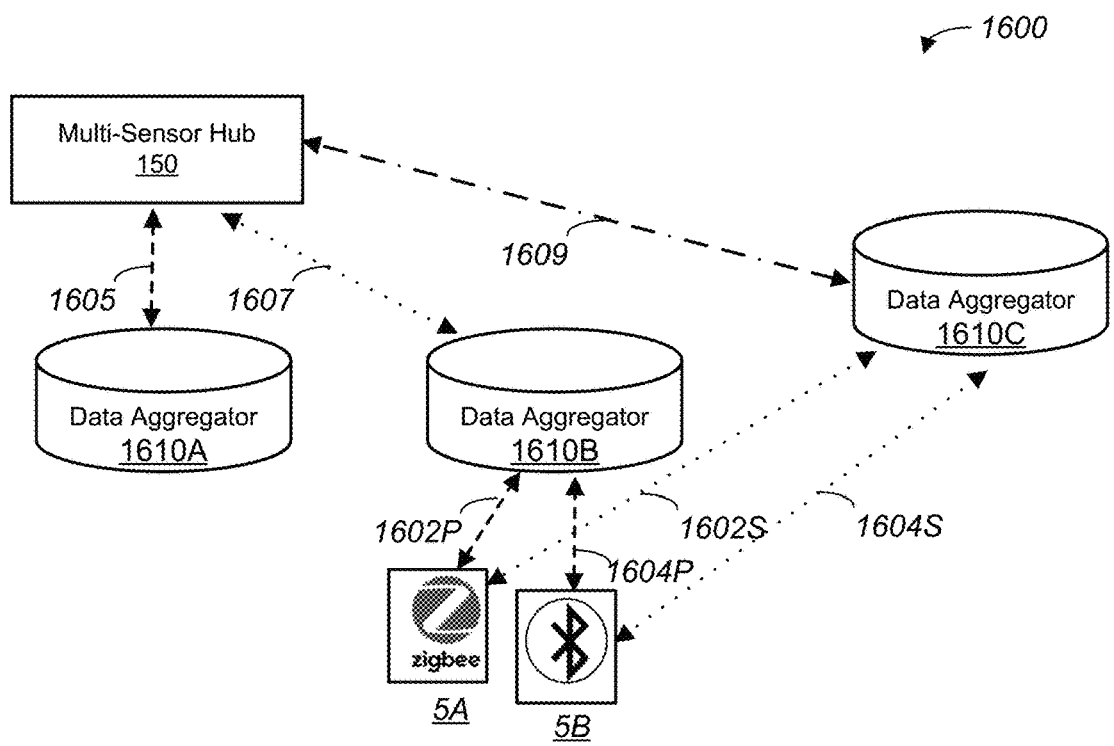

FIGS. 16A and 16B illustrate a process for altering a data path of one or more devices in a network 1600, according to one or more aspects of the present disclosure. The network 1600 can be similar to or the same as one or more networks discussed herein. In one or more embodiments, the network 1600 includes a multi-sensor hub 150, a plurality of data aggregators 1610, such as data aggregators 1610A, 1610B and 1610C, one or more sensing devices 5, such as a Zigbee capable sensing device 5A and a Bluetooth capable sensing device 5B, or any combination thereof. In one or more embodiments, a data aggregator 1610 can be a multi-sensor device 140. The data aggregators 1610A, 1610B, and 1610C are connected to the multi-sensor hub 150, for example, via connections 1605, 1607, and 1609. The data aggregators 1610 are capable of receiving data from the sensing devices 5 using various protocols, including, but not limited to, Zigbee and Bluetooth.

FIG. 16A illustrates that sensing devices 5A and 5B have a primary connection 1602P and 1604P in a network 1600, respectively, to the data aggregator 1610A and a secondary connection 1602S and 1604S, respectively, to data aggregator 1610B. Connections 1602P and 1602S utilize the Zigbee protocol while connections 1604P and 1604S utilize the Bluetooth protocol. Sensing devices 5A and 5B are only paired to data aggregator 1610A with data aggregator 1610B being designated as a back-up in case of failure of the data aggregator 1610A. While FIGS. 16A and 16B illustrate the Zigbee protocol and Bluetooth protocol, the present disclosure contemplates any one or more short-range protocols.

FIG. 16B illustrates that the primary connections 1602P and 1604P for sensing devices 5A and 5B, respectively, in a network 1600 have been switched from data aggregator 1610A to data aggregator 1610B and the secondary connections 1602S and 1604S for sensing devices 5A and 5B, respectively, have been switched from data aggregator 1610B to data aggregator 1610C. For example, the multi-sensor hub 150 can detect a failure at the primary data aggregator 1610A and determine that the primary connection associated with the sensing devices 5 should be switched to the secondary data aggregator 1610B. The multi-sensor hub 150 can determine that data aggregator 1610C is within range of the sensing device 5A and 5B such that data aggregator 1610C should be designated as the secondary data aggregator.

In one or more embodiments, any one or more of sensing devices 5A and 5B can be moved within the network 1600. For example, a sensing device 5A can be moved from a first room to a second room which places the sensing device 5A out of range of the primary data aggregator 1610A. The multi-sensor hub 150 can determine that the sensing device 5A has been moved and switch the secondary connection 1602S to the primary connection 1602P. In this way, the network 1600 is resilient such that data can be communicated to multi-sensor hub 150 regardless of the location of any particular sensing device.

Figure 17:
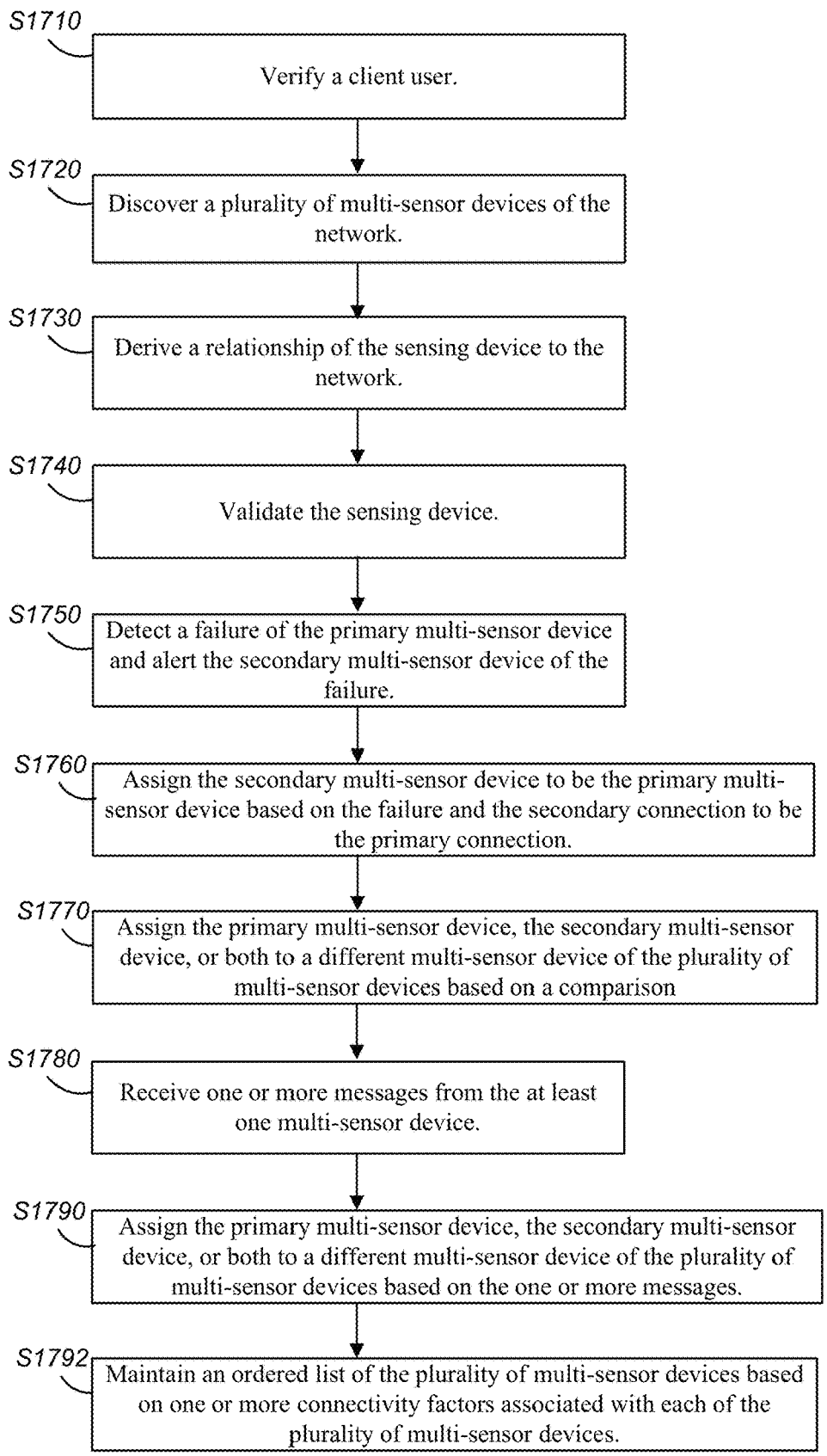
FIG. 17 is a flow chart illustrating a method for admitting a sensing device to a network, according to one or more aspects of the present disclosure.

FIG. 17 is a flow chart illustrating a method for admitting a sensing device 5 to a network, according to one or more aspects of the present disclosure. A multi-modal portal system 18 and/or a multi-sensor hub 150 may be programmed with one or more instructions that when executed by a processor controller causes the multi-modal portal system 18 and/or the multi-sensor hub 150 to admit a sensing device 5 to a network after a validation and to ensure redundancy in data paths from the sensing device 5 to a multi-sensor device 140 (or data aggregator) so that data can be received by a multi-sensor hub 150 for communication to the multi-modal portal system 18, according to one or more embodiments. In FIG. 17, it is assumed that any one or more of the network devices include their respective controllers and their respective software stored in the respective memories, as discussed herein in connection with any one or more figures, such as FIGS. 1, 3-11, 13, 14, 15, and 16 which when executed by their respective controllers perform the functions and operations in accordance with the example embodiments of the present disclosure (e.g., including providing a video notification to a client user).

The multi-modal portal system 18 and/or the multi-sensor hub 150 comprises a controller 26 that executes one or more computer-readable instructions, stored on a memory 24, that when executed perform one or more of the operations of steps S1710-1792. The multi-modal portal system 18 and/or the multi-sensor hub 150 can comprise one or more software 25, for example, a multi-modal portal application 350 or other software. For example, any one or more steps of FIG. 17 can be implemented via the analytics engine 302, the access portal 306, or both of the multi-modal portal application 350, software 25 of the multi-sensor hub 150, or any combination thereof. While the steps S1710-S1792 are presented in a certain order, the present disclosure contemplates that any one or more steps can be performed simultaneously, substantially simultaneously, repeatedly, in any order or not at all (omitted).

At step S1710, a multi-sensor hub 150 for admitting a sensing device 5 to a network verifies a client user (such as client user 410 or 420) associated with the multi-sensor hub 150 of the network. For example, the client user may be required to enter one or more login credentials via the multi-sensor hub 150. The client user can be verified based on an associated profile configuration 250. In one or more embodiments, the multi-sensor hub 150 requests verification from the multi-modal portal system 18 connected to the multi-sensor hub 150.

At step S1720, the multi-sensor hub 150 discovers a plurality of multi-sensor devices 140 of the network. At least one multi-sensor device of the plurality of multi-sensor devices 140 is coupled to the multi-sensor hub 150. In one or more embodiments, the at least one multi-sensor device is coupled or connected directly to the multi-sensor hub 150. In one or more embodiments, any one or more of the plurality of multi-sensor devices 140 are coupled to the multi-sensor hub 150 using any one or more protocols other than a wireless connection protocol.

At step S1730, the multi-sensor hub 150 derives a relationship of the sensing device 5 to the network. For example, a sensing device 5 can be transitioned throughout a site such that the sensing device 5 disconnects from and attempts to reconnect to the network as the sensing device 5 is transitioned. For example, the sensing device 5 can be moved from one room of a client user's home to another room. In one or more embodiments, the sensing device 5 is associated with a particular user as indicated by a profile configuration 250 associated with a client user based on a user identifier 2660 of the client user. For example, a device identifier 508 can be associated with the sensing device 5 and information associated with the device identifier 508 can be used to derive a relationship of the sensing device 5 to the network, for example, as discussed with reference to FIG. 8.

At step S1740, the multi-sensor hub 150 validates the sensing device 5. In one or more embodiments, validating the sensing device 5 comprises determining a first multi-sensor device of the plurality of multi-sensor devices 140 as a primary multi-sensor device based on the relationship, associating the sensing device 5 with the primary multi-sensor device via a primary connection, determining a second multi-sensor device of the plurality of multi-sensor devices 140 as a secondary multi-sensor device based on the relationship, associating the sensing device with the secondary multi-sensor device via a secondary connection 160, and admitting the sensing device 5 to the network. The primary connection and the secondary connection can be associated as discussed with reference to FIGS. 16A and 16B.

At step S1750, the multi-sensor hub 150 detects a failure of the primary multi-sensor device and alerts the secondary multi-sensor device of the failure. In one or more embodiments, the failure is indicative of a loss of power at the primary multi-sensor device, a lack of response or communication with the primary multi-sensor device within a time threshold or time lapse, disconnection of the primary multi-sensor device from the network, maintenance or other activity that disrupts communication with the primary multi-sensor device, any other failure, or any combination thereof.

At step S1760, the multi-sensor hub 150 assigns the secondary multi-sensor device to be the primary multi-sensor device based on the failure and assigns the secondary connection to be the primary connection. For example, the multi-sensor hub 150 automatically switches the secondary multi-sensor device to be the primary multi-sensor device which also switches the secondary connection to be the primary connection. In this way, the network connections of the network are resilient such that a failure does not disrupt communication of data from one or more sensing devices to the multi-sensor hub 150. In one or more embodiments, after the switch, a third multi-sensor device of the plurality of multi-sensor devices is determined to be the secondary multi-sensor device, for example, the new secondary multi-sensor device.

At step S1770, the multi-sensor hub 150 assigns the primary multi-sensor device, the secondary multi-sensor device, or both to a different multi-sensor device of the plurality of multi-sensor devices based on a comparison. For example, the multi-sensor hub 150 can monitor one or more connectivity factors associated with the plurality of multi-sensor devices and compares the one or more connectivity factors to a corresponding one or more thresholds. The assigning is then based on this comparison. In one or more embodiments, the one or more connectivity factors comprise a distance from a multi-sensor device to the multi-sensor hub 150 and the one or more thresholds comprise a maximum distance between a multi-sensor device and the multi-sensor hub 150. The distance from the multi-sensor device to the multi-sensor hub 150 can be determined by the multi-sensor hub 150 based on a number of hops or any other measurement. This distance can then be compared to a corresponding threshold to determine whether or not a particular multi-sensor device should be assigned as a primary multi-sensor device, a secondary multi-sensor device or both.

At step S1780, the multi-sensor hub 150 receives one or more messages from the at least one multi-sensor device. The messages can be indicative of a status of one or more of the plurality of multi-sensor devices 140. For example, the at least one multi-sensor device can receive a status indicator from any one or more other multi-sensor devices of the plurality of multi-sensor devices 140. The status indicator can comprise any one or more of one or more connectivity factors, a power indicator, any other indicator, or a combination thereof. At step S1790, the multi-sensor hub 150 assigns the primary multi-sensor device, the secondary multi-sensor device, or both to a different multi-sensor device based on the one or more messages. For example, the multi-sensor hub 150 can determine based on the one or more messages that a more efficient path exists for connectivity between of the plurality of multi-sensor devices and the multi-sensor hub 150 or another multi-sensor device of the plurality of multi-sensor devices.

At step S1792, the multi-sensor hub 150 maintains an ordered list of the plurality of multi-sensor devices of the network based on one or more connectivity factors associated with each of the plurality of multi-sensor devices. In one or more embodiments, the multi-sensor hub 150 can periodically or at timed intervals scan or poll the plurality of multi-sensor devices. The scan or poll can return the one or more connectivity factors or one or more messages as discussed with respect to step S1780. The multi-sensor hub 150 can order the multi-sensor devices based on the one or more connectivity factors. For example, the multi-sensor hub 150 can order the multi-sensor devices based on a distance, a signal strength, or both such that if a failure is detected, the multi-sensor hub 150 can switch or assign a multi-sensor device to be a primary multi-sensor device or a secondary multi-sensor device based on the ordered list. In one or more embodiments, the ordered list is updated manually, for example, by any of the multi-modal portal system 18, a user associated with the profile configuration 250, any other factor, or a combination thereof.

While the present disclosure discusses an aging-in-place environment, the present disclosure contemplates any other environment that requires remote monitoring be provided within a secure and private network environment such that on-demand and/or pre-authorized can be provided as well as an audit trail or log can be maintained.

According to one or more example embodiments of inventive concepts disclosed herein, there are provided novel solutions for configuring one or more network devices automatically using one or more configuration values retrieved from a network resource where the one or more configuration values are associated with one or more configuration parameters associated with the network device. The novel solutions according to example embodiments of inventive concepts disclosed herein provide features that enhance the installation and configuration of home/residential network gateway (GW) devices, wireless fidelity access points (Wi-Fi APs), Home Network Controller (HNC) devices, wireless routers, mesh networking nodes (e.g., Wi-Fi EasyMesh systems), and the like by providing automatic and dynamic configuration of network devices based on configuration values that can be verified, updated and stored in a network resource, such as a webform stored in a repository.

Each of the elements of the present invention may be configured by implementing dedicated hardware or a software program on a memory controlling a processor to perform the functions of any of the components or combinations thereof. Any of the components may be implemented as a CPU or other processor reading and executing a software program from a recording medium such as a hard disk or a semiconductor memory, for example. The processes disclosed above constitute examples of algorithms that can be affected by software, applications (apps, or mobile apps), or computer programs. The software, applications, computer programs or algorithms can be stored on a non-transitory computer-readable medium for instructing a computer, such as a processor in an electronic apparatus, to execute the methods or algorithms described herein and shown in the drawing figures. The software and computer programs, which can also be referred to as programs, applications, components, or code, include machine instructions for a programmable processor, and can be implemented in a high-level procedural language, an object-oriented programming language, a functional programming language, a logical programming language, or an assembly language or machine language.

The term "non-transitory computer-readable medium" refers to any computer program product, apparatus or device, such as a magnetic disk, optical disk, solid-state storage device (SSD), memory, and programmable logic devices (PLDs), used to provide machine instructions or data to a programmable data processor, including a computer-readable medium that receives machine instructions as a computer-readable signal. By way of example, a computer-readable medium can comprise DRAM, RAM, ROM, EEPROM, CD-ROM or other optical disk storage, magnetic disk storage or other magnetic storage devices, or any other medium that can be used to carry or store desired computer-readable program code in the form of instructions or data structures and that can be accessed by a general-purpose or special-purpose computer, or a general-purpose or special-purpose processor. Disk or disc, as used herein, includes compact disc (CD), laser disc, optical disc, digital versatile disc (DVD), floppy disk and Blu-ray disc. Combinations of the above are also included within the scope of computer-readable media.

The word "comprise" or a derivative thereof, when used in a claim, is used in a nonexclusive sense that is not intended to exclude the presence of other elements or steps in a claimed structure or method. As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise. Use of the phrases "capable of," "configured to," or "operable to" in one or more embodiments refers to some apparatus, logic, hardware, and/or element designed in such a way to enable use thereof in a specified manner.

While the principles of the inventive concepts have been described above in connection with specific devices, apparatuses, systems, algorithms, programs and/or methods, it is to be clearly understood that this description is made only by way of example and not as limitation. The above description illustrates various example embodiments along with examples of how aspects of particular embodiments may be implemented and are presented to illustrate the flexibility and advantages of particular embodiments as defined by the following claims, and should not be deemed to be the only embodiments. One of ordinary skill in the art will appreciate that based on the above disclosure and the following claims, other arrangements, embodiments, implementations and equivalents may be employed without departing from the scope hereof as defined by the claims. It is contemplated that the implementation of the components and functions of the present disclosure can be done with any newly arising technology that may replace any of the above-implemented technologies. Accordingly, the specification and figures are to be regarded in an illustrative rather than a restrictive sense, and all such modifications are intended to be included within the scope of the present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What I claim is:

1. A multi-sensor hub for admitting a sensing device of one or more sensing devices to a network comprising:
   a memory storing one or more computer-readable instructions; and
   a processor configured to execute the one or more computer-readable instructions to:
      verify a client user associated with the sensing device and the multi-sensor hub based on a profile configuration associated with the client user, wherein verifying the client user comprises requested verification from a multi-modal portal system connected to the multi-sensor hub;
      discover a plurality of multi-sensor devices of the network, wherein at least one multi-sensor device of the plurality of multi-sensor devices is associated with the client user, and wherein the multi-sensor hub receives data from the one or more sensing devices directly or indirectly via one or more multi-sensor devices of the plurality of multi-sensor devices;
      derive a relationship of the sensing device to the network based on a device identifier, of the profile configuration, associated with the sensing device; and
      validate the sensing device, wherein validating the sensing device comprises:
         determining a first multi-sensor device of the plurality of multi-sensor devices as a primary multi-sensor device based on the relationship, wherein the first multi-sensor device is connected to the multi-sensor hub;
         associating the sensing device with the primary multi-sensor device via a primary connection so as to provide a first sensor data path for data associated with the sensing device to the multi-sensor hub;
         determining a second multi-sensor device of the plurality of multi-sensor devices as a secondary multi-sensor device based on the relationship, wherein the second multi-sensor device is connected to the multi-sensor hub;
         associating the sensing device with the secondary multi-sensor device via a secondary connection so as to provide a second sensor data path for data associated with the sensing device to the multi-sensor hub; and
         admitting the sensing device to the network.

2. The multi-sensor hub of claim 1, wherein the processor is further configured to execute the one or more instructions to:
   detect a failure of the primary multi-sensor device; and
   alert the secondary multi-sensor device of the failure.

3. The multi-sensor hub of claim 2, wherein the processor is further configured to execute the one or more instructions to:
   assign the secondary multi-sensor device to be the primary multi-sensor device based on the failure; and
   assign the secondary connection to be the primary connection.

4. The multi-sensor hub of claim 3, wherein the processor is further configured to execute the one or more instructions to:
   determine a third multi-sensor device of the plurality of multi-sensor devices as the secondary multi-sensor device.

5. The multi-sensor hub of claim 1, wherein the processor is further configured to execute the one or more instructions to:
   monitor one or more connectivity factors associated with the plurality of multi-sensor devices;
   compare the one or more connectivity factors to a corresponding one or more thresholds; and
   assign the primary multi-sensor device, the secondary multi-sensor device, or both to a different multi-sensor device of the plurality of multi-sensor devices based on the comparison.

6. The multi-sensor hub of claim 1, wherein the processor is further configured to execute one or more instructions to:
   receive one or more messages from the at least one multi-sensor device, wherein the one or more messages are indicative of a status of one or more of the plurality of multi-sensor devices; and assign the primary multi-sensor device, the secondary multi-sensor device, or both to a different multi-sensor device of the plurality of multi-sensor devices based on the one or more messages.

7. The multi-sensor hub of claim 1, wherein the processor is further configured to execute one or more instructions to:
maintain an ordered list of the plurality of multi-sensor devices based on one or more connectivity factors associated with each of the plurality of multi-sensor devices.

8. A method for admitting a sensing device of one or more sensing devices to a network by a multi-sensor hub, the method comprising:
verifying a client user associated with the sensing device and the multi-sensor hub based on a profile configuration associated with the client user, wherein verifying the client user comprises requested verification from a multi-modal portal system connected to the multi-sensor hub;
discovering a plurality of multi-sensor devices of the network, wherein at least one multi-sensor device of the plurality of multi-sensor devices is associated with the client user, and wherein the multi-sensor hub receives data from the one or more sensing devices directly or indirectly via one or more multi-sensor devices of the plurality of multi-sensor devices;
deriving a relationship of the sensing device to the network based on a device identifier, of the profile configuration, associated with the sensing device; and
validating the sensing device, wherein validating the sensing device comprises:
determining a first multi-sensor device of the plurality of multi-sensor devices as a primary multi-sensor device based on the relationship, wherein the first multi-sensor device is connected to the multi-sensor hub;
associating the sensing device with the primary multi-sensor device via a primary connection so as to provide a first sensor data path for data associated with the sensing device to the multi-sensor hub;
determining a second multi-sensor device of the plurality of multi-sensor devices as a secondary multi-sensor device based on the relationship, wherein the second multi-sensor device is connected to the multi-sensor hub;
associating the sensing device with the secondary multi-sensor device via a secondary connection so as to provide a second sensor data path for data associated with the sensing device to the multi-sensor hub; and
admitting the sensing device to the network.

9. The method of claim 8, further comprising:
detecting a failure of the primary multi-sensor device; and
alerting the secondary multi-sensor device of the failure.

10. The method of claim 9, further comprising:
assigning the secondary multi-sensor device to be the primary multi-sensor device based on the failure; and
assigning the secondary connection to be the primary connection.

11. The method of claim 10, further comprising:
determining a third multi-sensor device of the plurality of multi-sensor devices as the secondary multi-sensor device.

12. The method of claim 8, further comprising:
monitoring one or more connectivity factors associated with the plurality of multi-sensor devices;
comparing the one or more connectivity factors to a corresponding one or more thresholds; and assigning the primary multi-sensor device, the secondary multi-sensor device, or both to a different multi-sensor device of the plurality of multi-sensor devices based on the comparison.

13. The method of claim 8, further comprising:
receiving one or more messages from the at least one multi-sensor device, wherein the one or more messages are indicative of a status of one or more of the plurality of multi-sensor devices; and
assigning the primary multi-sensor device, the secondary multi-sensor device, or both to a different multi-sensor device of the plurality of multi-sensor devices based on the one or more messages.

14. The method of claim 8, further comprising:
maintaining an ordered list of the plurality of multi-sensor devices based on one or more connectivity factors associated with each of the plurality of multi-sensor devices.

15. A non-transitory computer-readable medium of a multi-sensor hub storing one or more instructions for admitting a sensing device of one or more sensing devices to a network, which when executed by a processor of the multi-sensor hub, cause the multi-sensor hub to perform one or more operations comprising:
verifying a client user associated with the sensing device and the multi-sensor hub based on a profile configuration associated with the client user, wherein verifying the client user comprises requested verification from a multi-modal portal system connected to the multi-sensor hub;
discovering a plurality of multi-sensor devices of the network, at least one multi-sensor device of the plurality of multi-sensor devices is associated with the client user, and wherein the multi-sensor hub receives data from the one or more sensing devices directly or indirectly via one or more multi-sensor devices of the plurality of multi-sensor devices;
deriving a relationship of the sensing device to the network; and
validating the sensing device, wherein validating the sensing device comprises:
determining a first multi-sensor device of the plurality of multi-sensor devices as a primary multi-sensor device based on the relationship, wherein the first multi-sensor device is connected to the multi-sensor hub;
associating the sensing device with the primary multi-sensor device via a primary connection so as to provide a first sensor data path for data associated with the sensing device to the multi-sensor hub;
determining a second multi-sensor device of the plurality of multi-sensor devices as a secondary multi-sensor device based on the relationship, wherein the second multi-sensor device is connected to the multi-sensor hub;
associating the sensing device with the secondary multi-sensor device via a secondary connection so as to provide a second sensor data path for data associated with the sensing device to the multi-sensor hub; and
admitting the sensing device to the network.

16. The non-transitory computer-readable medium of claim 15, wherein the one or more instructions when executed by the processor further cause the multi-sensor hub to further perform the one or more operations comprising:
detecting a failure of the primary multi-sensor device; and
alerting the secondary multi-sensor device of the failure.

17. The non-transitory computer-readable medium of claim 16, wherein the one or more instructions when executed by the processor further cause the multi-sensor hub to further perform the one or more operations comprising:
assigning the secondary multi-sensor device to be the primary multi-sensor device based on the failure; and
assigning the secondary connection to be the primary connection; and
determining a third multi-sensor device of the plurality of multi-sensor devices as the secondary multi-sensor device.

18. The non-transitory computer-readable medium of claim 15, wherein the one or more instructions when executed by the processor further cause the multi-sensor hub to further perform the one or more operations comprising:
monitoring one or more connectivity factors associated with the plurality of multi-sensor devices;
comparing the one or more connectivity factors to a corresponding one or more thresholds; and
assigning the primary multi-sensor device, the secondary multi-sensor device, or both to a different multi-sensor device of the plurality of multi-sensor devices based on the comparison.

19. The non-transitory computer-readable medium of claim 15, wherein the one or more instructions when executed by the processor further cause the multi-sensor hub to further perform one or more operations comprising:
receiving one or more messages from at least one multi-sensor device, wherein the one or more messages are indicative of a status of one or more of the plurality of multi-sensor devices; and
assigning the primary multi-sensor device, the secondary multi-sensor device, or both to a different multi-sensor device of the plurality of multi-sensor devices based on the one or more messages.

20. The non-transitory computer-readable medium of claim 15, wherein the one or more instructions when executed by the processor further cause the multi-sensor hub to further perform one or more operations comprising:
maintaining an ordered list of the plurality of multi-sensor devices based on one or more connectivity factors associated with each of the plurality of multi-sensor devices.

* * * * *